(12) United States Patent
Niestroj et al.

(10) Patent No.: US 7,144,856 B2
(45) Date of Patent: *Dec. 5, 2006

(54) INHIBITORS OF DIPEPTIDYL PEPTIDASE I

(75) Inventors: Andre Niestroj, Halle/Saale (DE); Ulrich Heiser, Halle/Saale (DE); Hans-Ulrich Demuth, Halle/Saale (DE)

(73) Assignee: Probiodrug AG, Halle (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/997,821

(22) Filed: Nov. 24, 2004

(65) Prior Publication Data

US 2005/0233978 A1    Oct. 20, 2005

Related U.S. Application Data

(63) Continuation of application No. 10/236,136, filed on Sep. 6, 2002, now Pat. No. 6,844,316.

(60) Provisional application No. 60/340,150, filed on Dec. 14, 2001.

(30) Foreign Application Priority Data

Sep. 6, 2001    (DE)    ................ 101 43 840

(51) Int. Cl.
A61K 38/05     (2006.01)
C07K 5/06      (2006.01)

(52) U.S. Cl. .................... 514/2; 514/19; 530/300; 560/312; 560/315

(58) Field of Classification Search .................. None
See application file for complete search history.

(56) References Cited

U.S. PATENT DOCUMENTS

| | | | |
|---|---|---|---|
| 2,961,377 A | 11/1960 | Shapiro et al. ................ 167/65 |
| 3,174,901 A | 3/1965 | Sterne ........................ 167/65 |
| 3,879,541 A | 4/1975 | Kabbe et al. ................ 424/326 |
| 3,960,949 A | 6/1976 | Ahrens et al. ........... 260/564 B |
| 4,028,402 A | 6/1977 | Fischer et al. ......... 260/501.14 |
| 4,935,493 A | 6/1990 | Bachovchin et al. ....... 530/331 |
| 5,433,955 A | 7/1995 | Bredehorst et al. ......... 424/94.3 |
| 5,462,928 A | 10/1995 | Bachovchin et al. ......... 514/19 |
| 5,512,549 A | 4/1996 | Chen et al. .................... 514/12 |
| 5,543,396 A | 8/1996 | Powers et al. ................ 514/19 |
| 5,552,426 A | 9/1996 | Lunn et al. ................ 514/394 |
| 5,614,379 A | 3/1997 | MacKellar ................ 435/68.1 |
| 5,624,894 A | 4/1997 | Bodor ........................ 514/2 |
| 5,705,483 A | 1/1998 | Galloway et al. ............. 514/12 |
| 5,827,898 A | 10/1998 | Khandwala et al. ........ 514/734 |
| 5,939,560 A | 8/1999 | Jenkins et al. ............. 548/535 |
| 6,006,753 A | 12/1999 | Efendic ...................... 128/898 |
| 6,011,155 A | 1/2000 | Villhauer .................... 544/333 |
| 6,077,822 A * | 6/2000 | Dyrsting et al. ................ 514/8 |
| 6,107,317 A | 8/2000 | Villhauer .................... 514/365 |
| 6,110,949 A | 8/2000 | Villhauer .................... 514/365 |
| 6,124,305 A | 9/2000 | Villhauer .................... 514/272 |
| 6,172,081 B1 | 1/2001 | Damon ........................ 514/307 |
| 6,201,132 B1 | 3/2001 | Jenkins et al. ............. 548/535 |
| 6,303,661 B1 | 10/2001 | Demuth et al. ............. 514/866 |
| 6,319,893 B1 | 11/2001 | Demuth et al. ................ 514/2 |
| 6,448,282 B1 | 9/2002 | Phillips et al. ............. 514/400 |
| 6,500,804 B1 | 12/2002 | Demuth et al. ............... 514/19 |
| 6,517,824 B1 | 2/2003 | Kohn et al. ............. 424/78.06 |
| 6,548,481 B1 | 4/2003 | Demuth et al. ................ 514/19 |
| 6,605,589 B1 | 8/2003 | Uckun et al. .................. 514/2 |
| 6,844,316 B1 * | 1/2005 | Niestroj et al. ................. 514/2 |
| 2001/0025023 A1 | 9/2001 | Carr ............................. 514/2 |

FOREIGN PATENT DOCUMENTS

| | | |
|---|---|---|
| DE | 25 42 598 | 4/1976 |
| DE | 25 42 598 A1 | 4/1976 |
| DE | 296 075 | 11/1991 |

(Continued)

OTHER PUBLICATIONS

Translation of DE 198 34 610 (Feb. 24, 2000).*

(Continued)

*Primary Examiner*—Jeffrey Edwin Russel
(74) *Attorney, Agent, or Firm*—Sonnenschein Nath & Rosenthal LLP

(57) ABSTRACT

The present invention relates to specific inhibitors of the cysteine protease dipeptidyl peptidase I (DP I)which can be used in the treatment of malignant cell degeneration, immune diseases impaired wound healing and metabolic diseases of humans and are represented by the general formula

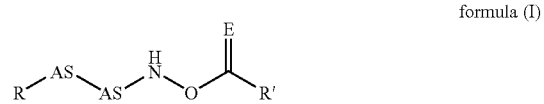

formula (I)

and the pharmaceutical salts thereof, in which R is a peptide or a branched or unbranched $C_1$–$C_9$ alkyl chain, a branched or unbranched $C_2$–$C_9$ alkenyl chain, a branched or unbranched $C_2$–$C_9$ alkynyl chain, a $C_3$–$C_9$ cycloalkyl, $C_4$–$C_9$ carbocyclic, $C_5$–$C_{14}$ aryl, $C_3$–$C_9$ heteroaryl, $C_3$–$C_9$ heterocyclic, all of the above residues optionally being substituted, the residue AS—AS is a dipeptide or a mimetic thereof, AS is an amino acid or a peptide mimetic thereof. The amino acid is peptide bound with R and R' is a branched or unbranched $C_1$–$C_9$ alkyl chain, a branched or unbranched $C_2$–$C_9$ alkenyl chain, a branched or unbranched $C_2$–$C_9$ alkynyl chain, a $C_3$–$C_9$ cycloalkyl, $C_4$–$C_9$ cycloalkenyl, $C_2$–$C_9$ heterocycloalkyl, $C_3$–$C_9$ heterocycloalkenyl, $C_5$–$C_{14}$ aryl, $C_3$–$C_9$ heteroaryl, $C_3$–$C_9$ heterocyclic, whereas the heterocycloalkyl, heterocycloalkenyl, heteroaryl, heterocyclic residue can have up to 6 hetero ring atoms, an amino acid or a peptide mimetic thereof, all of the above residues may be optionally substituted, or is H.

20 Claims, No Drawings

FOREIGN PATENT DOCUMENTS

| | | |
|---|---|---|
| DE | 296 075 A5 | 11/1991 |
| DE | 196 16 486 | 10/1997 |
| DE | 196 16 486 C2 | 10/1997 |
| DE | 299 09 210 U | 9/1999 |
| DE | 299 09 210 | 10/1999 |
| DE | 198 26 972 | 12/1999 |
| DE | 198 26 972 A1 | 12/1999 |
| DE | 198 34 610 | 2/2000 |
| DE | 198 34 610 A1 | 2/2000 |
| EP | 0 658 568 | 6/1995 |
| EP | 0 658 568 A1 | 6/1995 |
| EP | 0 708 179 | 4/1996 |
| EP | 0 708 179 A2 | 4/1996 |
| EP | 0 995 440 | 4/2000 |
| EP | 0 995 440 A1 | 4/2000 |
| EP | 1 130 022 | 9/2001 |
| EP | 1 130 022 A1 | 9/2001 |
| FR | 2 085 665 | 12/1971 |
| FR | 2.085.665 | 12/1971 |
| FR | 2 696 740 | 4/1994 |
| FR | 2 696 740 A1 | 4/1994 |
| JP | 04-288098 | 10/1992 |
| JP | 04-334357 | 11/1992 |
| JP | 4334357 | 11/1992 |
| WO | WO 91/11457 | 8/1991 |
| WO | WO 91/16339 | 10/1991 |
| WO | WO 91/17767 | 11/1991 |
| WO | WO 93/01812 | 2/1993 |
| WO | WO 93/08259 | 4/1993 |
| WO | WO 93/20061 | 10/1993 |
| WO | WO 95/11689 | 5/1995 |
| WO | WO 95/15309 | 6/1995 |
| WO | WO 95/22327 | 8/1995 |
| WO | WO 95/29691 | 11/1995 |
| WO | WO 97/40832 | 11/1997 |
| WO | WO 97/45117 | 12/1997 |
| WO | WO 98/19998 | 5/1998 |
| WO | WO 98/22494 | 5/1998 |
| WO | WO 99/41220 | 8/1999 |
| WO | WO 99/41224 | 8/1999 |
| WO | WO 99/46272 | 9/1999 |
| WO | WO 99/46272 A | 9/1999 |
| WO | WO 99/61431 | 12/1999 |
| WO | WO 99/62914 | 12/1999 |
| WO | WO 00/01849 | 1/2000 |
| WO | WO 00/10549 | 3/2000 |
| WO | WO 00/53171 | 9/2000 |
| WO | WO 00/53596 | 9/2000 |
| WO | WO 00/58360 | 10/2000 |
| WO | WO 00/58360 A3 | 10/2000 |
| WO | WO 01/09169 | 2/2001 |
| WO | WO 01/09169 A2 | 2/2001 |
| WO | WO 01/32624 | 5/2001 |
| WO | WO 01/32624 A1 | 5/2001 |
| WO | WO 01/34594 | 5/2001 |
| WO | WO 01/34594 A1 | 5/2001 |
| WO | WO 01/62266 | 8/2001 |
| WO | WO 01/62266 A2 | 8/2001 |
| WO | WO 01/74299 | 10/2001 |
| WO | WO 01/74299 A2 | 10/2001 |
| WO | WO 01/89569 | 11/2001 |
| WO | WO 01/89569 A1 | 11/2001 |
| WO | WO 01/94310 | 12/2001 |
| WO | WO 01/94310 A1 | 12/2001 |
| WO | WO 01/97808 | 12/2001 |
| WO | WO 02/13821 | 2/2002 |
| WO | WO 02/13821 A1 | 2/2002 |
| WO | WO 02/20825 | 3/2002 |
| WO | WO 02/20825 A1 | 3/2002 |
| WO | WO 03/016335 | 2/2003 |
| WO | WO 03/016335 A2 | 2/2003 |
| WO | WO 03/070732 | 8/2003 |
| WO | WO 03/070732 A1 | 8/2003 |
| WO | WO 04/089366 A1 | 10/2004 |
| WO | WO 2004/089366 | 10/2004 |

OTHER PUBLICATIONS

Campbell, I. W. *New Antidiabetic Drugs*, ed. C.J. Bailey & P.R. Flatt, Smith-Gordon, "Sulphonylureas and metformin: efficacy and inadequacy". 3:33-51 (1990).

*Chemical Abstracts*, vol. 115. No. 15, Oct. 14, 1991 Columbus, Ohio, US; abstract No. 149947q, Schoen Ekkehard et al: "Dipeptidyl peptidase IV in the immune system. Effects of specific enzyme inhibitors on activity of dipeptidyl peptidase IV and proliferation of human lymphocytes".

*Chemical Abstracts*, vol. 118, No. 25, Jun. 21, 1993 Columbus, Ohio, US; abstract No. 255342k, Hosoda, et al, "Preparation of N-(heterocyclic Carbonyl) Amino Acids and Analogs as Prolyl Endopeptidase Inhibitors", Nov. 1992 (Nov. 20, 1992).

*Chemical Abstracts*, vol. 126, No. 2, Jan. 13, 1997 Columbus, Ohio, US; abstract No.16161j, Stoeckel A. et al: "Competitive inhibition of proline specific enzymes by amino acid thioxopyrrolidides and thiazolidides".

*Martindale The Extra Pharmacopoeia*, 30th Edition, London Pharmaceutical Press, 1993, p. 1619.

Amasheh, S., et al., "Electrophysiological analysis of the function of the mammalian renal peptide transporter expressed in Xenopus Laevis oocytes". *J. Physiol.* 504, 169-174 (1997).

Arai et al., "Synthesis of prolyl endopeptidase inhibitors and evaluation of their structure-activity relationships : in vitro inhibition of prolyl endopeptidase from Canine Brain" *Chemical and Pharmaceutical Bulletin.*, Bd. 41, No. 9, 1993, pp. 1583-1588.

Durinx, C.; et al.; "Reference Values for Plasma Dipepidyl-Pepidase IV activity and their Association with Other Laboratory Parameters". *Clin Chem Lab Med 2001*, Feb.; 39 (2) :155-9, 1 page.

Gossrau, R.; "Cytochemistry of Membrane Proteases". *Histochem J*, Jul. 1985; 17 (7) :737-71, 1 page.

Hahn, T.; et al.; "Enzyme Histochemical Evidence for the Presence of Potential Blood Pressure Regulating Proteases in Cultured Villous Explants from Human First Trimester Placentae". *Acta Histochem* Dec. 1993, 95 (2): 185-92, 1 page.

Heymann, et a., "Has Dipeptidyl Peptidase IV an Effect on Blood Pressure and Coagulation." *Klin Wochenschr*, Jan. 1984, 2;62 (1) : 2-10, 1 page.

J. Lin et al.: "Inhibition of depeptidyl peptidase IV by fluoroolefin-containing n-peptidyl-O-hydroxylamine peptidomimetics" *Proceedings of the National Academy of Sciences of USA*, vol. 95, Nov. 1998, pp. 14020-14024.

Korom, S., et al "Inhibition of CD26/dipeptidyl peptidase IV activity in vivo prolongs cardiac allograft survival in rat recipients", *Transplantation*, vol. 63, 1495-1500 No. 10 (1997).

Magyar, C.E. et al., "Proximal Tubule Na Transporter Responses are the same during Acute and Chronic Hypertension." *Am. J. Physiol Renal Physiol*, Aug. 2000; 279 (2) :F358-69, 1 page.

*Martindale The Extra Pharmacopoeia*, 30th Edition, London Pharmaceutical Press, 1993, p. 36.

Mentlein, R., et al., "Proteolytic processing of neuropeptide Y and peptide YY by dipeptidyl peptidase IV". *Regul. Pept.* 49, 133-144 (1993).

Papies, B. et al., "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." *Cor Vasa*, 1991; 33 (3) :218-26, 1 page.

Qureshi. N.U.; et al., "Endogenous Neuropeptide Y Mediates Vasoconstriction during Endotoxic and Hemorrhagic Shock". *Regul Pept*, Sep. 25, 1998, 25; 75-76:215-20, 1 page.

Tanaka, S., et al., "Suppression of arthritis by the inhibitors of dipeptidyl peptidase IV". *Int. J. Immunopharmacol*, vol. 19, No. 1 pages 15-24, (1997).

*The Merck Index*, 11th Edition, *An Encyclopedia of Chemicals, Drugs*, and Biologicals, 1989, p. 934.

*The Merck Index*, 12th Edition, *An Encyclopedia of Chemicals, Drugs*, and Biologicals, 1996, p. 1014.

Deacon et al., *Journal of Clinical Endocrinology and Metabolism*, "Degradation of Glucagon-Like Peptide-1 by Human Plasma in Vitro Yields and N-Terminally Truncated Peptide That Is A Major Endogenous Metabolite in Vivo", (1995), 80(3): 952-957.

G.G. Duncan, *Diseases of Metabolism (Asian edition)*, "Diabetes Mellitus", (1966), p. 951-957.

Gutniak et al., *Diabetes Care*, "Subcutaneous Injection of the Incretin Hormone Glucagon-Like Peptide 1 Abolishes Postprandial Glycemia in NIDDM", Sep. 1994, 17(9): 1039-1044.

Gutniak et al., *New England Journal of Medicine*, "Antidiabetogenic Effect of Glucagon-like peptide-1 (7-36) Amide in Normal Subjects and Patients With Diabetes Mellitus", 1992, 326: 1326-1322.

H.A. Smith et al., *Veterinary Pathology* (fourth edition), "Diseases and Disorders of Metabolism: Deficiency Diseases", (1972), p. 1018-1020.

Hendrick et al., *Metabolism—Clinical and Experimental*, "Glucagon-like Peptide-I-(7-37) Suppresses Hyperglycemia in Rats", Jan. 1993, 42(1): 1-6.

Hoffmann et al., *Journal of Chromatography A*, "Inhibition of dipeptidyl peptidase IV (DP IV) by anti-DP IV antibodies and non-substrate X-X-Pro- oligopeptides ascertained by capillary eletrophoresis", 1995, 716:355-362.

Index Nominum, *International Drug Directory 1992/1993*, Medpharm Scientific Publishers, pp. 728-729.

Mannucci et al., *Diabetes Care*, "Effect of Metformin on Glucagon-Like Peptide 1 (GLP-1) and Leptin Levels in Obese Nondiabetic Subjects", 24(3): 489-494, Mar. 2001.

Nauck et al., *Diabetologia*, "Normalization of fasting hyperglycaemia by exogenous glucagon-like peptide 1 (7-36 amide) in Type 2 (non-insulin-dependent) diabetic patients", (1993), 36: 741-744.

Pauly et al., *Regulatory Peptides*, "Abstracts Issue: Abstracts from the 11$^{th}$ International Symposium on Regulatory Peptides", Jul. 15, 1996, 64(1-3): 148 plus cover.

Stryer, *Biochemistry 3$^{rd}$ Ed.*, "Protein Conformation, Dynamics, and Function", 1988, p. 191-193.

T.J. Kieffer et al., "Degradation of Glucose-Dependent Isulinotropic Polypeptide and Truncated Glucagon-Like Peptide 1 In Vitro and In Vivo by DP IV", *Endocrinology*, vol. 136(8), (1995), p. 3583-3596.

The Merck Index, *An Encyclopedia of Chemicals and Drugs*, 9$^{th}$ Edition, Merck & Co., Inc., 1976, p. 773.

Welch, C.B., *Medical Management of Non-Insulin-Dependent (Type II) Diabetes*, 3$^{rd}$ edition, American Diabetes Association, "Diagnosis and Classification" p. 3, 1994, Pharmacological Intervention (2 pages).

Wetzel, W., et al., "Effects of the CLIP fragment ACTH 20-24 on the duration of REM sleep episodes". *Neuropeptides*, 31, 41-45 (1997).

Willms et al., *Journal of Clinical Endocrinology Metabolism*, "Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients", 1996, 81(1): 327-332.

Ashworth et al., *Bioorg. Med. Chem. Lett.*, "2-Cyanopyrrolidides as Potent, Stable Inhibitors of Dipeptidyl Peptidase IV", (1996), 6(10): 1163-1166.

Badia-Elder N.E. et al., *Alcoholism Clinical and Experimental Research*, "Effects of Neuropeptide Y (NPY) on Ethanol Intake and Anxiety in High and Low Alcohol Drinking (HAD1/LAD1) Rats", (2000), 24(5): 82A.

C.F. Deacon et al., *Diabetes*, "Both Subcutaneously and Intravenously Administered Glucagon-Like Peptide I Are Rapidly Degraded from the NH$_2$-Terminus in Type II Diabetic Patients and in Healthy Subjects", Sep. 1995, 44: 1126-1131.

Edwards, J. V. et al., *J. Peptide Res.*, "Synthesis and Activity of NH$_2$ - and COOH-Terminal Elastase Recognition Sequences on Cotton," (1999), 54: 536-543.

Endroczi et al., *ACTA Physiol. Hung.*, "Dipeptidyl peptidase IV (DP IV) and Superoxide Dismutase Activity in Thymus-Derived Lymphocytes: Effects of Inhibitory Pepdides and Zn$^{2+}$ in Vitro", (1990), 75(1): 35-44.

Frohman et al., *Journal of Clin. Invest.*, "Rapid Enzymatic Degradation of Growth Hormone-releasing Hormone by Plasma in Vitro and in Vivo to a Biologically Inactive Product Cleaved at the NH$_2$ Terminus", vol. 78, Oct. 1986, p. 906-913.

*Goodman & Gilman's The Pharmacological Basis of Therapeutics*, Ninth Edition, (1996), p. 1510.

Lee, H.S. et al., "Cathepsin B Inhibitory Peptides Derived from β-Casein," *Peptides* 21 (2000) 807-809.

Nathan et al., *Diabetes Care*, "Insulinotropic Action of Glucagon-like Peptide-1-(7-37) in Diabetic and Nondiabetic Subjects", Feb. 1992, 15(2): 270-275.

Pauly et al., *Metabolism*, "Improved Glucose Tolerance in Rats Treated with the Dipeptidyl Peptidase IV (CD26) Inhibitor Ile-Thiazolidide", (1999), 48(3): 385-389.

Pschyrembel, Kininisches Wörterbuch 257, Auflage, (1994), 9 pages.

Snow et al., *Advances In Medicinal Chemistry*, "Boronic Acid Inhibitors of Dipeptidyl Peptidase IV: A New Class of Immunosuppressive Agents", vol. 3, (1995), p. 149-177.

Thorens et al., *Diabetes*, "Glucagon-Like Peptide-I and the Control of Insulin Secretion in the Normal State and in NIDDM", (1993), 42:1219-1225.

Vidal, (1993), 69$^{th}$ Edition, p. 612-613.

Wakselman et al., "Inhibition of HIV-1 infection of CD 26$^{30}$ but not CD 26$^-$ cells by a potent cyclopeptidic inhibitor of the DPP IV activity of CD26", Abstract p. 44 of the 24$^{th}$ *European Peptide Symposium*, (1996).

Wettstein, J.G. et al. *Pharmacology & Therapeutics*, "Central Nervous System Pharmacology of Neuropeptide Y.", (1995), 65(3): 397-414.

Bergmeier, Stephen C., *Tetrahedron, Elsevier Science Ltd.*, "The Synthesis of Vicinal Amino Alcohols", vol. 56, No. 17, (2000), pp. 2561-2576.

Kowamoto et al., *Tetrahedron Asymmetry, Elsevier Science Ltd.*, "Enantioselective Synthesis of β-Hydroxy Amines and Aziridines Using Asymmetric Transfer Hydrogenation of α-Amido Ketones", vol. 11, No. 16 (2000), pp. 3257-3261.

Munglani R. et al., Drugs, *Adis International Ltd*, At, "The Therapeutic Potential of Neuropeptide Y Analgesic, Anxiolytic and Antihypertensive", (1996) 52(3): 371-389.

Orskov, Catherine et al., "Proglucagon Products in Plasma of Noninsulin-dependent Diabetics and Nondiabetic Controls in the Fasting State and after Oral Glucose and Intravenous Arginine" *J. Clin. Invest.*, vol. 87, 1991, pp. 415-423.

Reinhold, D. et al., *Journal of Neuroimmunology*, "Inhibitors of Dipeptidyl Peptidase IV/CD26 Suppress Activation of Human MBP-Specific CD4 + T Cell Clones", (1998) 87: 203-209.

Sengupta, et al., *Tetrahedron Letters, Elsevier Science Ltd.* "Amino Acid Derived Morpholine Amides for Nucleophilic α-Amino Acylation Reactions: A New Synthetic Route to Enantiopure α-Amino Ketones", vol. 40, No. 21 (1999), pp. 4107-4110.

Stöckel-Maschek, A., et al., *Biochimica et Biophysica Acta*, "Thioxo Amino Acid Pyrrolidides and Thiazolidides: new Inhibitors of Proline Specific Peptidases", (2000) 1479: 15-31.

Stryer, Lubert, *Biochemistry*, "Amino Acid Degradation and the Urea Cycle" (1975) pp. 451-452.

Mentlein et al., *Eur. J. Biochem*, Dipeptidyl-Peptidase IV Hydrolyses Gastric Inhibitory Polypeptide, Glucagon-Like Peptide-1(7-36)Amide, Peptide Histidine Methionine and is Responsible for Their Degradation in Human Serum. (1993), 214, pp. 829-835.

Augustyns et al., *Eur. J. Med. Chem.*, "Pyrrolidides: Synthesis and Structure-Activity Relationship as Inhibitors of Dipeptidyl Peptidase IV", (1997), vol. 32, pp. 301-309.

Wen-Tien Chen et al. "Seprase Complexes in Cellular Invasiveness", *Cancer and Metastasis Reviews* 22: 259-269, (2003).

Victor A. Gault et al., "Glucose-Dependent Insulinotropic Polypeptide Analogues and Their Therapeutic Potential for the Treatment of Obesity-Diabetes", *Biochemical and Biophysical Research Communications* 308: 207-213, (2003).

Lader, Malcolm H., MD, "Assessment Methods and the Different Diagnosis of Anxiety", *Journal of Clinical Psychopharmacology*, (1981), vol. 1, No. 6, pp. 342-349.

Winslow, R., "Novartis Drug Alters Picture for Diabetes" *Wall Street Journal*, Wed., Dec. 27, 2000, p. B2.

Ansorge, S., et al., "Membrane-bound peptidases of lymphocytes: Functional implications", Biomed. Biochim, Acta 50 (1991) 4-6, pp. 799-807.

Dodge, R. W., et al., "Folding and Unfolding Kinetics of the Proline-to-Alanine Mutants of Bovine Pancreatic Ribonuclease A," Biochemistry 1996, 35, pp. 1548-1559.

Demuth, Hans-Ulrich, "Recent Developments in Inhibiting Cysteine and Serine Proteases", J. Enzyme Inhibition, 1990, vol. 3, pp. 249-278.

Gomez, S., et al., "Relationship between endo- and exopeptidases in a processing enzyme system: Activation of an endoprotease by the aminopeptidase B-like activity in somatostatin-28 convertase", Proc. Natl. Acad. Sci. USA, vol. 85 pp. 5468-5472, Aug. 1988.

Hegen, M., et al., "The T Cell Triggering Molecule Tp103 is Associated with Dipeptidyl Aminopeptidase IV Activity," The Journal of Immunology, vol. 144, pp. 2908-2914, No. 8, Apr. 15, 1990.

Ishiura, S., et al., "Identification of a putative amyloid A4-generating enzyme as a prolyl endopeptidase," Federation of European Biochemical Societies, vol. 260, No. 1, pp. 131-134, Jan. 1990.

Kräusslich, Hans-Georg, et al., "Viral Proteinases", Ann. Rev. Biochem. 1988, 57 pp. 791-754.

Pederson, R.A., et al., "Improved Glucose Tolerance in Zucker Fatty Rats by Oral Administration of the Dipeptidyl Peptidase IV Inhibitor Isoleucine Thiazolidide", Diabetes, vol. 47, Aug. 1998 pp. 1253-1258.

Vanhoof, G., et al., "Proline motifs in peptides and their biological processing", The FASEB Journal, vol. 9, Jun. 1995, pp. 736-744.

Walter, R., et al., "Proline Specific Endo- and Exopeptidases", Molecular & Cellular Biochemistry, vol. 30, No. 2, Apr. 18, 1980, pp. 111-127.

Kessler, Von Horst, "Konformation und biologische Wirkung von cyclischen Peptiden", Angew. Chem. 94 (1982) pp. 509-520.

Kirschke, H. et al., "Proteinases 1: Lysosomal Cysteine Proteinases" Protein Profile, vol. 2, Issue 14, 1995, pp. 1583-1634.

Yaron, A., et al., "Proline-Dependent Structural and Biological Properties of Peptides and Proteins" Critical Reviews in Biochemistry and Molecular Biology, 28(1), pp. 31-81 (1993).

Vallee et al., "Larval Development of Tribolium Confusum in the Presence of Non-Naturally Occurring Amino Acids", Database CAPLUS on STN, Accession No.: 1963:75103, Annales de l'ACFAS (1962), 28, p. 26-27 (abstract).

Holst, J. et al., "Inhibition of the Activity of Dipeptidyl-Peptidase IV as a Treatment for Type 2 Diabetes", Diabetes, 47, 11, Heatlh & Medical Complete pp. 1663-1670, Nov. 1998.

Shaw, Michael K. et al. "Cysteine and Serine Protease Inhibitors Block Intracellular Development and Disrupt the Secretory Pathway of Toxoplasma gondii" Microbes and Infection, 4, pp. 119-132 (2002).

Brömme, Dieter et al., "N-Peptidyl-O-Carbamoyl Amino Acid Hydroxamates: Irreversible Inhibitors for the Study of the $S_2$' Specificity of Cysteine Proteinases", Federation of European Biochemical Societies Letters, vol. 322, No. 3, pp. 211-214, (1993).

Brachwitz, Hans, "Hydroximino Acid Derivatives. IV. 3-Acyl-1, 2, 4-Oxadiazoles From N-Acyl-and N-Ethoxycarbonyl-.Alpha.-Amino Ketones", CAPLUS, 76:113134 (1972).

Gault et al., "Characterization of Cellular and Metabolic Effects of a Novel Enzyme-Resistant Antagonist of Glucose-Dependent Insulinotropic Polypeptide", Biochemical and Biophysical Research Communications 290, 1420-1426 (2002).

Hinke et al., "Dipeptidyl Peptidase IV-Resistant [D-Ala$^2$]Glucose-Dependent Insulinotropic Polypeptide (GIP) Improves Glucose Tolerance in Normal and Obese Diabetic Rats", Diabetes, vol. 51: 652-661 (2002).

Hinke et al., Identification of a Bioactive Domain in the Amino-Terminus of Glucose-Dependent Insulinotropic Polypeptide (GIP), Biochimica et Biophysica Acta 1547, 143-155 (2001).

Kuhn-Wache et al., "Analogs of Glucose-Dependent Insulinotropic Polypeptide With Increased Dipeptidyl Peptidase IV Resistance", Cellular Peptidases in Immune Functions and Diseases 2, 187-195 (2000).

Hinke et al., "Further Development of Antidiabetic Enzyme Resistant Incretin Analogues", Diabetologia, pp. 176, (2002).

Schilling et al., "Glutaminyl Cyclases Unfold Glutamyl Cyclase Activity Under Mild Acid Conditions", FEBS Letters 563, 191-196 (2004).

Misquitta et al., "Inhibition Studies of Glutaminyl Cyclase", FASEB Journal (Federation of American Societies for Experimental Biology), vol. 15, No. 5, pp. A1159 (2001).

Misquitta et al., "Characterization of the Inhibition of Glutaminyl Cyclase By Imidazole Derivatives and Phenanthrolines", FASEB Journal (Federation of American Societies for Experimental Biology), vol. 16, No. 4, pp. A157 (2002).

Ganellin et al. "Design of Potent Non-Thiourea $H_3$-Receptor Histamine Antagonists", J. Med. Chem. vol. 38, pp. 3342-3350 (1995).

Liu et al., "Nonpeptide Somatostatin Agonists with $sst_4$ Selectivity: Synthesis and Structure-Activity Relationships of Thioureas", J. Med. Chem., vol. 41, pp. 4693-4705 (1998).

Wright et al., "Thromboxane Synthetase Inhibitors and Antihypertensive Agents. 4. N-[(1H-Imidazol-l-yl)alkyl] Derivatives of Quinazoline-2,4(1H,3H)-diones, Quinazolin-4(3H)-ones, and 1,2,3-Benzotriazin-4(3H)-ones", J. Med. Chem., vol. 30, pp. 2277-2283 (1987).

Clader et al., "Substituted (1,2-Diarylethyl)amide Acyl-CoA:Cholesterol Acyltransferase Inhibitors: Effect of Polar Groups on in Vitro and in Vivo Activity", J. Med. Chem., vol. 38, pp. 1600-1607 (1995).

Venkatachalam et al., "Anti-HIV Activity of Aromatic and Heterocyclic Thiazolyl Thiourea Compounds", Bioorganic & Medicinal Chemistry Letters, vol. 11, pp. 523-528 (2001).

Moon et al., "Cholinergic Activity of Acetylenic Imidazoles and Releated Compounds", J. Med. Chem., vol. 34, pp. 2314-2327 (1991).

Wright et al., "Thromboxane Synthetase Inhibitors and Antihypertensive Agents. 1. N-[(1H-Imidazol-1-yl)alkyl] aryl Amides and N-[(1H-1,2,4-Triazol-1-yl)alkyl]aryl Amides", J. Med. Chem., vol. 29, pp. 523-530 (1986).

Amasheh, et al.; "Electrophysiological analysis of the function of the mammaliam renal peptide transporter expressed in Xenopus laevis oocytes"; Journal of Physiology; (1997); 504(1): 169-174.

Ansorge, et al.; "Membrane-bound peptidases of lymphocytes; Functional implications"; Biomed. Biochim. Acta; (1991); 50(4-6); 799-807.

Arai, et al. "Synthesis of Prolyl Endopeptidase Inhibitors and Evaluation of Their Structure-Activity Relationships: In Vitro Inhibition of Prolyl Endopeptidase from Canine Brain"; Chem. Pharm. Bull.; (1993); 41(i): 1583-1588.

Ashworth, et al.; "2-Cyanopyrrolidides as Potent, Stable Inhibitors of Dipeptidyl Peptidase IV"; Bioorganic & Medicinol Chemistry Letters; (1996); 6(10): 1163-1166.

Augustyns, et al.; "Pyrrolidides: synthesis and structure-activity relationship as inhibitors or dipeptidyl peptidase IV"; Eur. J. Ed. Chem.; (1997); 32: 301-309.

Badia-Elder, et al; "Effects of Neuropeptide (NPY) on Ethanol Intake and Anxiety in High and Low Alcohol Drinking (Hadi/Ladi) rats"; Purdue School of Science; (2000).

Bergmeier; "The Synthesis of Vivinal Amino Alcohols"; Tetrahedron; (2000); 56: 2561-2576.

Welch, et al.; "Medical Management of Non-Insulin-Dependent (Type II) Diabetes"; ADA—Third Edition; (1994); 3-4.

Campbell, et al.; "Sulphonylureas and metformin: efficacy and inadequacy"; New Antidiabetic Drugs; (1990); 33-51.

Chemical Abstract 115; 1-Pharmacology; (1991); 115: 37.

Chemical Abstract 118; 34-Amino Acids, Peptides, Proteins; (1993); 118: 933.

Chemical Abstract 126; 7-Enzymes; (1997); 126(2): 241.

Deacon, et al.; "Both Subcutaneously and Intravenously Administered Glucagon-Like Peptide I are Rapidly Degraded from the $NH_2$-Terminus in Type II Diabetic Patients and in Healthy Subjects"; Diabetes : (1995); 4: 1126-1131.

Deacon, et al.; "Degradation of Glucagon-Like Peptide-1 by Human Plasma in Vitro Yields an N-Terminally Truncated Peptide that is a Major Endogenous Metabolite in Vivo"; J. of Clinical Endocrinology and Metabolism; (1996); 80: 952-957.

Dodge, et al.; "Folding and Unfolding Kinetics of the Proline-to-Alanine Mutants of Bovine Pancreatic Ribonuclease A\"; *Biochemistry*; (1996); 35: 1548-1559.

Duncan; "Diseases of Metabolism: Detailed Methods of Diagnosis and Treatment"; (1964); 951-957.

Durinx, et al.; "Reference values for plasma dipeptidyl-peptidase IV activity and their association with other laboratory parameters"; *Clin. Chem. Lab. Med.*; (2001); 39(2): 155-159.

Edwards, et al.; "Synthesis and activity of $NH_2$- and COOH-terminal elastase recognition sequences on cotton"; *J. Peptide Res.*; (1999); 54: 536-543.

Endroczi, et al.; "Dipeptidyl Peptidase IV (DP IV) and Superoxide Dismutase Activity in Thymus-Derived Lymphocytes: Effects of Inhibitory Peptides and $ZN^{2+}$ In Vitro"; *Acta Physiologica Hungarian* (1996); 75(1): 35-44.

Frohman, et al.; "Rapid Enzymatic Degradation of Growth Hormone-releasing Hormone by Plasma In Vitro and In Vivo to a biologically Inactive Product Cleaved at the $NH_2$ Terminus"; *J. Clin. Invest.*; (1986); 78: 906-913.

Gomez, et al.; "Relationship between endo- and expopeptidases in a processing enzyme system: Activation of an endoprotease by the aminopeptidase B-like activity in somatostatin-28 convertase"; *Proc. Natl. Acad. Sci. USA*; (1988); 85: 5468-5472.

Goodman & Gilman's; "Hormone and Hormone Antagonists"; *The Pharmacological Basis of Therapeutics Ninth Edition*; (1996); 1510.

Gossrau; "Cytochemistry of membrane proteases"; *Histochem J.*; (1985) 17(7): 737-71.

Gutniak, et al.; "Antidiabetogenic Effect of Glucagon-Like Peptide-1 (7-36) Amide in Normal Subjects and Patients with Diabetes Mellitus"; *New England J. Med.*; (1992); 326: 1316-1322.

Gutniak, et al.; "Subcutaneous Injection of the Incretin Hormone Glucagon-Like Peptide 1 Abolishes Postprandial Glycemia in NIDDM"; *Diabetes Care*; (1994); 17(9): 1039-1044.

Hahn, et al.; "Enzyme histochemical evidence for the presence of potential blood pressure regulating proteases in cultured villous explants from human first trimester placentae"; *Acta Histochem*; (1993); 95(2): 185-92.

Demuth; "Recent Developments in Inhibiting cysteine and Serine Proteases"; *J. Enzyme Inhibition*; (1990); 3: 249-278.

Hegen, et al.; "The T Cell Triggering Molecule Tp103 is Associated with Dipeptidyl Aminopeptidase IV Activity"; *The Journal of Immunology*; (1990); 144(8): 2908-2914.

Hendrick, et al.; "Glucagon-like Peptide-1-(7-37) Suppresses Hyperglycemia in Rats"; *Metabolism Clinical and Experimental*; (1993); 42(1): 1-6.

Heymann & Mentlein; "Has dipeptidyl peptidase IV an effect on blood pressure and coagulation"; *Klin Wochenschr*; (1984); 62(1): 2-10.

Krausslich & Wimmer; "Viral Proteinases"; *Ann. Rev. Biochem.*; (1988); 57: 701-754.

Hoffmann, et al.; "Inhibition of dipeptidyl peptidase IV (DP IV) by anti-DP IV antibodies and non-substrate X-X-Pro- oligopeptides ascertained by capillary electrophoresis"; *Journal of Chromatography A*; (1995); 716: 355-362.

Holst & Deacon; "Perspectives in Diabetes: Inhibition of the Activity of Dipeptidyl-Peptidase IV as a Treatment for Type 2 Diabetes"; *Diabetes*; (1998); 47(11): 1663-1670.

Lee & Lee; "Cathepsin B inhibitory peptides derived from •-casein"; *Peptides*; (2000); 21: 807-809.

Index Nominum—International Drug Directory 92/93.

Ishiura, et al.; "Identification of a putative amyloid A4-generating enzyme as a prolyl endopeptidase"; *National Institute of Neuroscience*; (1990); 260(1): 131-134.

Kawamoto & Wills; "Enantioselective synthesis of •-hydroxy amines and aziridines using asymmetric transfer hydrogenation of •-amido ketones"; *tetrahedron: Asymmetry*; (2000); 11: 3257-3261.

Kessler; "Konformation und biologische Wirkung von cyclischem Peptiden"; *Angew Chem.*; (1982); 94: 509-520.

Kieffer, et al.; "Degradation of Glucose-Dependent Insulinotropic Polypeptide and Truncated Glucagon-Like Peptide 1 in Vitro and in Vivo by Dipeptidyl Peptidase IV"; *Endocrinology*; (1995); 136: 3585-3596.

Kirschke, et al.; "Proteinases 1: lysosomal cysteine proteinases"; *Protein Profile*; (1995); 2: 1587-1634.

Korom, et al.; "Inhibition of CD26/Dipeptidyl Peptidase IV Activity in Vivo Prolongs Cardiac Allograft Survival in Rat Recipients"; *Transplantation*, (1997); 54(10): 1495-1500.

Lader; "Assessment Methods and the Differential Diagnosis of Anxiety"; *Journal of Clinical Psychopharmacology*; (1981); 1(6): 342-349.

Lin, et al.; "Inhibition of dipeptidyl peptidase IV by fluoroolefin-containing N-peptidyl-O-hydrocylamine peptidomimetics"; *Proc. Nat. Acad. Sci. USA*; (1998); 95: 14020-14024.

Magyar, et al.; "Proximal rubule Na transporter responses are the same during acute and chronic hypertension"; *Am. J. Physiol. Renal. Physiol.*; (2000); 279(2) F358-369.

Mannucci, et al.; "Effect of Metformin on Glucagon-Like Peptide 1 (GLP-1) and Leptin Levels in Obese Nondiabetic Subjects"; *Diabetes Care*; (2001); 24(3): 489-494.

Martindale: The Extra Pharmacopoeia—Thirtieth Edition (1993) p. 1619.

Martindale: The Extra Pharmacopoeia—Thirtieth Edition (1993) p. 36.

Mentlein, et al.; "Proteolytic processing of neuropeptide Y and peptide YY by dipeptidyl peptidase IV"; *Regulatory Peptides*; (1993); 49: 133-144.

Mentlein, et al.; "Dipeptidyl-peptidase IV hydrolyses gastric inhibitory polypeptide, glucagon-like peptide-1(7-36)amide, peptide histidine methionine and is responsible for their degradation in human serum"; *Eur. J. Biochem.*; (1993); 214: 829-835.

Munglani, et al.; "The Therapeutic Potential of Neuropeptide Y"; *Review Article Cambridge University*; (1996); 371-389.

Nathan, et al.; "Insulinotropic Action of Glucagonlike Peptide-1-(7-37) in Diabetic and Nondiabetic Subjects"; *Diabetes Care*; (1991); 15(2): 270-276.

Nauck, et al.; "Normalization of fasting hyperglycaemia by exogenous glucagon-like peptide 1(7-36 amide) in Type 2 (non-insulin-dependent) diabetic patients"; *Diabetologia*; (1993); 741-744.

Orakov, et al.; "Proglucagon Products in Plasma of Noninsulin-dependent Diabetics and Nondiabetic Controls in the Fasting State and after Oral Glucose and Intravenous Arginine"; *J. Clin. Inves.*; (1991); 87: 415-423.

Papies, et al.; "Isoenzyme (lactate dehydrogenase, aspartate aminotransferase) and dipeptidyl peptidase IV activity changes in blood plasma likely indicative of organ involvement due to arterial hypertension"; *Cor Vasa*; (1991); 33(3): 218-26.

Pauly, et al.; "Improved Glucose Tolerance in Rats Treated with the Dipeptidyl Peptidase IV (CD26) Inhibitor Ile-Thiazolidide"; *Metabolism*; (1999); 48(3) 385-389.

Pauly, et al.; Abstracts Issue: Abstracts from the 11th International Symposium on Regulatory Peptides; *Regulatory Peptides*; (1996); 64(103): 148.

Pederson, et al.; "Improved glucose tolerance in Zucker fatty rats by oral administration of the dipeptidyl peptidase IV inhibitor isoleucine thiazolidide"; *Diabetes*; (1998); 47(8): 1253(6).

Pschyrembel Klinisches Worterbuch (1993).

Qureshi, et al.; "Endogenous neuropeptide Y mediates vasoconstriction during endotoxic and hemorrhagic shock"; *Regul. Pept.*; (1998) 75-76: 215-20.

Reinhold, et al.; "Inhibitors of dipeptidyl peptidase IV/CD26 suppress activation of human MBP-specific CD4 + T cell clones"; *Journal of Neuroimmunoloy*; (1998); 87: 203-209.

Sengupta, et al.; "Amino Acid Derived Morpholine Amides for Nucleophilic •-Amino Acylation Reactions: A New Synthetic Route to Enantiopure •-Amino Ketones"; *Tetrahedron Letters* (1999); 40: 4107-4110.

Smith, et al.; "Diseases and Disorders of Metabolism: Deficiency Diseases—Diabetes Mellitus"; *Veterinary Pathology*; (1972); 1018-1020.

Snow and Bachovchin; "Boronic Acid Inhibitors of Dipeptidyl Peptidase IV: A New Class of Immunosuppressive Agents"; *Advances in Medicinal Chemistry*; (1995); 3: 149-177.

Stockel-Maschek, et al.; "Thioxo amino acid pyrrolidides and thiazolidides: new inhibitors of proline specific peptidases"; *Ciochimmica et Biophysica Ata* (2000); 1479: 15-31.

Stryer; "Amino Acid Degradation and the Urea Cycle: Garrod's Discovery of Inborn Errors of Metabolism"; *Biochemistry*; (1975); 451-452.

Stryer; "Protein Conformation, Dynamics and Function"; *Biochemistry—Third Edition*; (1975); 191-193.

Tanaka, et al.; "Suppression of Arthritis by the Inhibitors of Dipeptidyl Peptidase IV"; *Int. J. Immunopharma*; (1997); 19(1) 15-24.

The Merck Index—Eleventh Edition; (1989); 934.

The Merck Index—Ninth Edition; (1976); 773.

The Merck Index—Twelfth Edition; (1996); 6000.

Thorens and Waeber; "Glucagon-Like Peptide-1 and the Control of Insulin Secretion in the Normal State and in NIDDM"; *Diabetes*; (1993); 42: 1219-1225.

Vallee and Martel; "Larval development of Tribolium confusum in the presence of non-naturally occurring amino acide"; *Annales de l'ACFAS*; (1962); 28: 26-27.

Gault, et al.; "Glucose-dependent insultinotropic polypeptide analogues and their therapeutic potential for the treatment of obesity-diabetes"; *BBRC*; (2003); 308: 207-213.

Vidal (1993) "Gluconate de Calcium Lavoisier".

Wakselman, et al.; "Inhibition of HIV-1 Infection of CD26$^+$ but not CD26 Cells by a Potent Cyclopeptidic Inhibitor of the DPP IV Activity of CD26"; *J. Med. Chem.*; (1993); 36: 1539.

Walter, et al.; "Proline Specific Endo-and Exopeptidases"; *Molecular & Cellular Biochemistry*; (1980); 30(2): 111-127.

Wetzel, et al.; "Effects of the CLIP fragment ACTH 20-24 on the duration of REM sleep episodes"; *Neuropeptides*; (1997); 31(1): 41-45.

Willms; et al; "Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients"; *J. of Clinical Endocrinology and Metabolism*; (1996); 81(1): 327-332.

Winslow; "Novartis Drug Alters Picture for Diabetes"; *The Wall Street Journal*; (2000); pp. B2.

Yaron and Naider; "Proline-Dependent Structural and Biological Properties of Peptides and Proteins"; *Critical Reviews in Biochemistry and Molecular Biology*; (1993); 28(1): 31-81.

Chen and Kelly; "Seprase Complexes in Cellular Invasiveness"; *Cancer and Metastasis Review*; (2003); 22: 259-269.

Wettstein, et al.; "Central Nervous System Pharmacology of Neuropeptide Y"; *Pharmac. Ther.*; (1995); 65: 397-414.

Vanhoof, et al. "Proline and Peptide Conformation"; *The FASEB Journal*; (1995); 9: 736-744.

Shaw, et al.; "Cystein and Serine Protease Inhibitors Block Intracellular Development and Disrupt the Secretory Pathway of Toxoplasma Gondii"; *Microbes and Infection*; (2002); 4: 119-132.

Bromme and Kurschke; "N-Peptidyl-O-Carbamoyl Amino Acid Hydroxamates: Irreversible inhibitors for the Study of the S2 Specificity of Cysteine Proteinases"; *FEBS*; (1993); 322(3): 211-214.

Brachwitz; "Hydroximino Acid Derivatives. IV. 3-Acyl-1,2,4-Oxadiazoles From N-Acyl and N-Ethoxycarbonyl-Alpha-Amino Ketones". *CAPLUS*; (1972); 76: 113134.

Gault, et al.; "Characterization of the Cellular and Metabolic Effects of a Novel Enzyme-Resistant Antagonist of Glucose-Dependent Insulinotropic Polypeptide"; *Biochemical and Biophysical Research Communications*; (2002); 290: 1420-1426.

Hinke, et al.; "Dipeptidyl Peptidase IV-Resistant [D-Ala$^2$]Glucose-Dependent Insulinotropic Polypeptide (GIP) Improves Glucose Tolerance in Normal and Obese Diabetic Rats"; *Diabetes*; (2002); 51: 652-661.

Hinke, et al.; Identification of a bioactive domain in the amino-terminus of glucose-dependent insulinotropic polypeptide (GIP); *Biochimica et Biophysical Acta*; (2001); 1547: 143-155.

Kuhn-Wache, et al.; "Analogs of Glucose-Dependent Insulinotropic Polypeptide with Increased Dipeptidyl Peptidase IV Resistance"; *Cellular Peptidase in Immune Functions and Diseases 2*; (2000); 187-195.

Schilling, et al.; "Glutaminyl cyclases unfold glutamyl cyclase activity under mild acid conditions"; *FEBS Letters*; (2004); 563: 191-196.

Misquitta, et al.; "Inhibition Studies of Glutaminyl Cyclase"; *FASEB Journal*; (2001); 15(5): A1159.

Misquitta, et al.; "Characterization of the Inhibitionof Glutaminyl cyclase by Imidazole Derivatives and Phenanthrolines"; *FASEB Journal*; (2002); 16(4): A157.

Ganellin,et al.; "Design of Potent Non-Thiourea H$_3$-Receptor Histamine Antagonists"; *J. Med. Chem.*; (1995); 38: 3342-3350.

Liu, et al.; "Nonpeptide Somatostatin Agonists with sst$_4$, Selectivity: Synthesis and Structure-Activity Relationships of Thioureas"; *J. Med. Chem.*; (1998); 41: 4693-4705.

Wright, et al.; "Thromboxane Synthetase Inhibitors and Antihypertensive Agents. 4. N[(1H-Imidazol-1-yl)alkyl] Derivatives of Quinazoline-2,4(1H,3H)-diones, Quinazolin-4(3H)-ones, and 1,2,3-Benzotriazin-4(3H)-ones"; *J. Med. Chem.*; (1987); 30: 2277-2283.

Clader, et al.; "Substituted (1,2-Diarylethyl) amide Acyl-CoA:Cholesterol Acyltransferase Inhibitors: Effect of Polar Groups on in Vitro and in Vivo Activity"; *J. Med. Chem.*; (1995); 38: 1600-1607.

Venkatachalam, et al.; "Anti-HIV Activity of Aromatic and Heterocyclic Thiazolyl Thiourea Compounds"; *Bioorganic & Medicinal Chemistry Letters*; (2001); 11: 523-528.

Moon, et al.; "Cholinergic Activity of Acetylenic Imidazoles and Related Compounds"; *J. Med. Chem.*; (1991); 34: 2314-2327.

Wright, et al.; "Thromboxane Synthetase Inhibitors and Antihypertensive Agents. 1. N-[(1H-Imidazol-1-yl)alkyl]aryl Amides and N-[(1H-1,2,4-Triazol-1-yl)alkyl]aryl Amides"; *J. Med. Chem.*; (1986); 29: 523-530.

Hinke, et al.; "Further Development of Antidiabetic Enzyme Resistant Incretin Analogues"; *Diabetologia*; (2002); pp. 176-177.

* cited by examiner

INHIBITORS OF DIPEPTIDYL PEPTIDASE I

CROSS REFERENCE TO RELATED APPLICATIONS

This application is a continuation of U.S. application Ser. No. 10/236,136 filed on Sep. 6, 2002 now U.S. Pat. No. 6,844,316, which claims priority to U.S. Provisional Application Ser. No. 60/340,150, filed on Dec. 14, 2001, and German Application Serial No. DE 101 43 840, filed on Sep. 6, 2001, which are incorporated herein by reference in their entirety.

FIELD OF THE INVENTION

The present invention relates to compounds that act as specific inhibitors of the cysteine protease dipeptidyl peptidase I (DP I). Compounds based on acylated hydroxamates are distinguished by being chemically stable in aqueous solutions, including biological fluids (Brömme & Demuth, 1994). Acylated hydroxamates are suicide inhibitors which deactivate the DP I by the reaction with the nucleophilic active site thiol residue.

BACKGROUND OF INVENTION

Dipeptidyl peptidase I is known to release active granulocyte serine proteases of lymphatic cells from their proforms. It participates in mechanisms that are used physiologically by cytotoxic lymphocytes in immune defence. In the case of pathophysiological processes such as malignant transformations of myeloid and lymphatic cells, the suppression of such mechanisms can be used for the treatment of carcinomas, immune diseases or metabolic diseases. The inhibitors of DP I according to the invention can be used for the treatment of such pathophysiological conditions and diseases.

In addition to proteases involved in non-specific proteolysis, which ultimately results in the breakdown of proteins into amino acids, regulatory proteases are known which take part in the functionalisation (activation, deactivation, modulation) of endogenous peptides (Kirschke et al., 1995; Kräusslich & Wimmer, 1987). In the immunological research and neuropeptide research, a number of such so-called convertases, signal peptidases or enkephalinases have been discovered (Gomez et al., 1988; Ansorge et al., 1991).

Dipeptidyl peptidase I (DP I, Peptidase Classification Clan CA, Family C1, IUBMB Enzyme Classification EC 3.4.14.1, CAS Registration No. 9032-68-2), formerly known as cathepsin C, was discovered in 1948 by Gutman & Fruton. DP I removes dipeptides sequentially from unsubstituted N-termini of polypeptide substrates with a relatively broad substrate specificity (McDonald et al., 1971; McDonald & Schwabe, 1977). DP I is a lysosomal cysteine protease which, by removing N-terminal dipeptides, is able to release active enzymes from proenzymes, such as granzyme A, granzyme B, leucocyte elastase, cathepsin B, neuraminidase, in the lysosomal granula of cytotoxic T-lymphocytes (Kummer et al., 1996; Thiele & Lipsky, 1997).

Therefore It is commonly assumed that the DP I is involved in pathological mechanisms such as apoptotic processes, muscular dystrophy and carcinogenesis (Aoyagi et al., 1983; Gelman et al., 1980; Schlangenauff et al., 1992; Shi et al., 1992).

DP I is known as the convertase of the blood-sugar-raising hormone glucagon which, in enzymatically reduced concentration, can lead to life-threatening hypoglycaemia (McDonald, J. K. et al., 1971).

Only weak inhibition of DP I is achieved by reversible and irreversible cysteine protease-inhibitors such as leupeptin and E-64, respectively (Nikawa et al., 1992). Stronger reversible inhibitors are stefin A and chicken cystatin, protein-inhibitors from the cystatin super-family, (Nicklin & Barrett, 1984); Specific inhibition has been achieved with the a prior reactive affinity labels of the diazomethyl ketone and sulphonylmethyl ketone type (Angliker et al., 1989; Green & Shaw, 1981; Hanzlik, R. P. & Xing, R., 1998). In the last few years, other new reversible DP I-inhibitors and irreversibly acting affinity labels of DP I have become known (Palmer et al., 1998; Thiele et al., 1997).

Such reversible inhibitors, which are able to display only short-term effects caused by diffusion processes, and the affinity labels that act irreversibly on the target enzyme in vitro but which, because of their chemically reactive radical which is present a priori, are able to react, prior to their interaction with the target enzyme, with other nucleophiles and electrophiles in biological fluids. Another type, mechanism-oriented inhibitors are distinguished by becoming catalytically attacked and activated only by the target enzyme. Such inhibitors are also known as suicide inactivators. Highly efficient suicide inactivators for cysteine proteases have been developed with the class of N-peptidyl, O-acyl hydroxylamines (Brömme et al., 1996). Inhibitors of DP I have not been derived from that class of compounds since DP I is inert towards typical irreversible cysteine protease-inhibitors known in the art, such as, for example, E-64.

Furthermore, N-terminally unprotected dipeptide derivatives tend towards rapid, intramolecular decomposition.

Inhibitors of DP I are described in WO9324634; U.S. Pat. No. 5,776,718; EP0995756; DE19834610; WO0220804; EP1188765, which are incorporated herein in their entirety concerning their structure, production and use.

Other helpful references include:

Ansorge, S., Schön, E., and Kunz, D. (1991). Membrane-bound peptidases of lymphocytes: functional implications. *Biomed. Biochim. Acta* 50, 799–807.

Angliker, H., Wikstrom, P., Kirschke, H., and Shaw, E. (1989). The inactivation of the cysteinyl exopeptidases cathepsin H and C by affinity labelling reagents. *Biochem. J.* 262, 63–68.

Aoyagi T., Wada, T., Kojima, F., Nagai, M., Miyoshino, S., and Umezawa, H. (1983). Two different modes of enzymatic changes in serum with progression of Duchenne muscular dystrophy. *Clin. Chim. Acta* 129, 165–173.

Brömme, D., Neumann, U., Kirschke, H., and Demuth, H.-U. (1996). Novel N-peptidyl-O-acyl hydroxamates: selective inhibitors of cysteine proteinases. *Biochim. Biophys. Acta.* 1202, 271–276.

Brömme, D., Demuth, H. U. (1994). N,O-Diacyl hydroxamates as selective and irreversible inhibitors of cysteine proteinases. *Methods in Enzym.* 244, 671–685.

Gelman B. B., Papa, L., Davis, M. H., and Gruenstein, E. (1980). Decreased lysosomal dipeptidyl aminopeptidase I activity in cultured human skin fibroblasts in Duchenne's muscular dystrophy. *J. Clin. Invest.* 65, 1398–1406.

Gomez, S., Gluschankof, P., Lepage, A., and Cohen, P. (1988). Relationship between endo- and exopeptidases in a processing enzyme system: activation of an endoprotease by the aminopeptidase B-like activity in somatostatin-28 convertase. *Proc Natl Acad Sci USA* 85, 5468–5472.

Green G. D. J. & Shaw, E. (1981). Peptidyl diazomethyl ketones are specific inactivators of thiol proteinases. *J. Biol. Chem.* 256, 1923–1928.

Gutman H. R. & Fruton, J. S. (1948). On the proteolytic enzymes of animal tissues VIII. An intracellular enzyme related to chymotrypsin. *J. Biol. Chem.* 174, 851–858.

Hanzlik, R. P. & Xing, R. (1998). Azapeptides as inhibitors and active site titrants for cysteine Proteinases. *J. Med. Chem.* 41, 1344–1351.

Kirschke, H., Barrett, A. J., and Rawlings, N. D. (1995). Proteinases 1: lysosomal cysteine proteinases. *Protein Profile* 2,1581–1643.

Kräusslich, H.-G. and Wimmer, E. (1987). Viral Proteinases. *Ann. Rev. Biochem.* 57, 701

Kummer, J. A., Kamp, A. M., Citarella, F., Horrevoets, A. J. G., and Hack, C. E. (1996). Expression of human recombinant granzyme A zymogen and its activation by the cysteine proteinase cathepsin C. *J. Biol. Chem.* 271, 9281–9286.

McDonald, J. K., Callahan, P. X., Ellis, S., and Smith, R. E. (1971). Polypeptide degradation by dipeptidyl aminopeptidase I (cathepsin C) and related peptidases. In: Tissue Proteinases (Barrett, A. J. & Dingle, J. T., eds). Amsterdam: North-Holland Publishing, pp. 69–107.

McDonald, J. K. & Schwabe, C. (1977). Intracellular exopeptidases. In: Proteinases in mammalian cells and tissues (Barrett, A. J., ed.). Amsterdam: North Holland Publishing, pp. 311–391.

Nicklin, M. J. H. & Barrett, A. J. (1984). Inhibition of cysteine proteinases and dipeptidyl peptidase I by egg-white cystatin. *Biochem. J.* 223, 245–253.

Nikawa, T., Towatari, T., and Katunuma, N. (1992). Purification and characterization of cathepsin J from rat liver. *Eur. J. Biochem.* 204, 381–393.

Palmer, J. T., Rasnick, D., and Klaus, J. L. (1998). Reversible protease inhibitors. U.S. Pat. No. 5,776,718

Schlagenauff, B., Klessen, C., Teichmann-Dörr, S., Breuninger. H., and Rassner, G. (1992). Demonstration of proteases in basal cell carcinomas. A histochemical study using amino acid-4-methoxy-2-naphthylamides as chromogenic substrates. Cancer 70, 1133–1140.

Shi, L., Kam, C.-M., Powers, J. C., Aebersold, R., and Greenberg, A. H. (1992). Purification of three cytotoxic lymphocyte granule serine proteases that induce apoptosis through distinct substrate and target cell interactions. *J. Exp. Med.* 176, 1521–1529.

Thiele, D. L., Lipsky, P. E., and McGuire, M. J. (1997). Dipeptidyl Peptidase-I inhibitors and uses thereof. U.S. Pat. No. 5,602,102

SUMMARY OF THE INVENTION

The invention relates to inhibitors of DPI having the general formula (I)

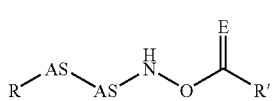

formula (I)

wherein

R is an acyl-residue including a urethane or peptide, or a branched or unbranched $C_1$–$C_9$ alkyl chain, a branched or unbranched $C_2$–$C_9$ alkenyl chain, a branched or unbranched $C_2$–$C_9$ alkynyl chain, a $C_3$–$C_9$ cycloalkyl, $C_4$–$C_9$ carbocyclic, $C_5$–$C_{14}$ aryl, $C_3$–$C_9$ heteroaryl, $C_3$–$C_9$ heterocyclic, all of the above residues optionally being substituted, or R is H, the residue AS-AS is a dipeptide or a mimetic thereof, E is O or S, and R' is a branched or unbranched $C_1$–$C_9$ alkyl chain, a branched or unbranched $C_2$–$C_9$ alkenyl chain, a branched or unbranched $C_2$–$C_9$ alkynyl chain, a $C_3$–$C_9$ cycloalkyl, $C_4$–$C_9$ cycloalkenyl, $C_2$–$C_9$ heterocycloalkyl, $C_3$–$C_9$ heterocycloalkenyl, $C_5$–$C_{14}$ aryl, $C_3$–$C_9$ heteroaryl, $C_3$–$C_9$ heterocyclic, wherein the heterocycloalkyl, heterocycloalkenyl, heteroaryl, heterocyclic residue can have up to 6 hetero atoms in the ring, or R' is an amino acid or a peptide or a mimetic thereof, all of the above residues optionally being substituted, or R' is H or alkoxy, alkenyloxy, alkynyloxy, carbocyclicoxy, heteroraryloxy, heterocyclicoxy, thioether or a substituted residue thereof or pharmaceutically acceptable salts thereof.

Examples of amino acids which can constitute the dipeptide AS-AS in the present invention are L and D-amino acids, N-methyl-amino-acids; alio- and threo-forms of Ile and Thr, which can, e.g. be α-, β- or ω-amino acids, whereof α-amino acids are preferred.

R' especially stands for H and for any alkyl, alkenyl, alkynyl, acyl, carbocyclic, aryl, heteroaryl, heterocyclic, alkoxy, alkenyloxy, alkynyloxy, carbocyclicoxy, heteroaryloxy, heterocyclicoxy, thioether or a substituted residue thereof.

The compounds according to the invention may also be in the form of prodrugs.

According to the invention, there are furthermore provided pharmaceutical compositions that comprise at least one compound according to the invention, optionally in combination with carriers and/or adjuncts etc. that are customary per se.

The compounds and compositions according to the invention can be used for the in vivo inhibition of the enzyme dipeptidyl peptidase I or of enzymes similar to DP I.

They can be used especially for the treatment of diseases of mammals that can be influenced by modulation of the DP I activity in various cells, tissues and organs.

They are especially suitable for the treatment of DPI-mediated malignant cell degeneration, immune diseases and metabolic diseases of humans.

The present invention further relates to the use of the compounds and compositions according to the invention for improving the wound-healing process and for the treatment of impaired wound-healing in humans.

DETAILED DESCRIPTION OF THE INVENTION

The invention relates to inhibitors of DP I having the general formula (I):

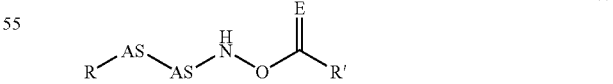

formula (I)

wherein

R is an acyl-residue including a urethane or peptide, or a branched or unbranched $C_1$–$C_9$ alkyl chain, a branched or unbranched $C_2$–$C_9$ alkenyl chain, a branched or unbranched $C_2$–$C_9$ alkynyl chain, a $C_3$–$C_9$ cycloalkyl, $C_4$–$C_9$ carbocyclic, $C_5$–$C_{14}$ aryl, $C_3$–$C_9$ heteroaryl, $C_3$–$C_9$ heterocyclic, all of the above residues optionally being substituted, or R is H, the residue AS—AS is a dipeptide or a mimetic thereof, E is O or S, and R' is a branched or unbranched $C_1$–$C_9$ alkyl chain, a branched or unbranched $C_2$–$C_9$ alkenyl chain, a branched or unbranched $C_2$–$C_9$ alkynyl chain, a $C_3$–$C_9$ cycloalkyl, $C_4$–$C_9$ cycloalkenyl, $C_2$–$C_9$ heterocycloalkyl, $C_3$–$C_9$ heterocycloalkenyl, $C_5$–$C_{14}$ aryl, $C_3$–$C_9$ heteroaryl, $C_3$–$C_9$ heterocyclic, wherein the heterocycloalkyl, heterocycloalkenyl, heteroaryl, heterocyclic residue can have up to 6 hetero atoms in the ring, or R' is an amino acid or a peptide or a mimetic thereof, all of the above residues optionally being substituted, or R' is H or alkoxy, alkenyloxy, alkynyloxy, carbocyclicoxy, heteroaryloxy, heterocyclicoxy, thioether or a substituted residue thereof or pharmaceutically acceptable salts thereof.

Examples of amino acids which can be used in the present invention are L and D-amino acids, N-methyl-amino-acids; allo- and threo-forms of Ile and Thr, which can, e.g. be α-, β- or ω-amino acids, whereof α-amino acids are preferred.

Preferably, the group AS—AS is bound with a peptide bond to R.

It has been found to be especially advantageous when the residue R is a phenyl or naphthyl residue that optionally is mono-, di-, or poly-substituted by $C_1$–$C_6$ alkyl, $C_2$–$C_6$ alkenyl, $C_2$–$C_6$ alkynyl, acyl, $C_1$–$C_6$ alkoxy, $C_2$–$C_6$ alkenyloxy, $C_2$–$C_6$ alkynyloxy, $C_3$–$C_9$ heteroaryloxy, $C_3$–$C_9$ heterocyclicoxy, $C_1$–$C_6$ thioether or a substituted residue thereof, $NO_2$, $NH_2$, F, Cl, Br, I atoms or groups. The above residues can be branched or unbranched.

It is especially preferred when R' is $NO_2$, $NH_2$, F, Cl, Br, I atoms or groups or is a phenyl or naphthyl residue, which is optionally mono-, di-, or poly-substituted by $C_1$–$C_6$ alkyl, $C_2$–$C_6$ alkenyl, $C_2$–$C_6$ alkynyl, $C_1$–$C_6$ acyl, $C_1$–$C_6$ alkoxy, $C_2$–$C_6$ alkenyloxy, $C_2$–$C_6$ alkynyloxy, $C_3$–$C_9$ heteroaryloxy, $C_3$–$C_9$ heterocyclicoxy, $C_1$–$C_6$ thioether or a substituted residue thereof, $NO_2$, $NH_2$, F, Cl, Br, I atoms or groups, or when R' is

wherein V is N or CH and n=1–6
or pharmaceutically acceptable salts thereof.

In a further preferred embodiment, compounds of formula (I) are provided,
wherein R' is

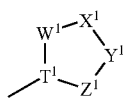

wherein $T^1$ is CH or N, $W^1$, $X^1$, $Y^1$ and $Z^1$ are independently from each other selected from $CH_2$, $NR^2$, $N^+(R^3)_2$, O, S, SO, $S(R^4)_2$, and $SO_2$ with the proviso that at least two or three of $W^1$, $X^1$, $Y^1$ and $Z^1$ are $CH_2$-groups, $R^2$, $R^3$ and $R^4$ are independently from each other a branched or unbranched $C_1$–$C_9$ alkyl chain, a branched or unbranched $C_2$–$C_9$ alkenyl chain, a branched or unbranched $C_2$–$C_9$ alkynyl chain, $C_3$–$C_9$ cycloalkyl, $C_4$–$C_9$ cycloalkenyl or H or pharmaceutically acceptable salts thereof.

In another illustrative embodiment, compounds of formula (I) are provided, wherein R' is

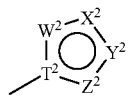

wherein $T^2$ is C or $N^+$, $W^2$, $X^2$, $Y^2$ and $Z^2$ are independently from each other CH, N,$N^+R^5$ or $S^+R^6$ with the proviso that at least two or three of $W^2$, $X^2$, $Y^2$ and $Z^2$ are $CH_2$-groups, $R^5$ and $R^6$ are independently from each other a branched or unbranched $C_1$–$C_9$ alkyl chain, a branched or unbranched $C_2$–$C_9$ alkenyl chain, a branched or unbranched $C_2$–$C_9$ alkynyl chain, $C_3$–$C_9$ cycloalkyl, $C_4$–$C_9$ cycloalkenyl or H or pharmaceutically acceptable salts thereof.

Furthermore, compounds of formula (I) are provided, wherein R' is

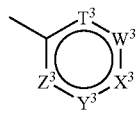

wherein $T^3$, $W^3$, $X^3$, $Y^3$ and $Z^3$ independently from each other are CH, $N^+R^7$ or $S^+R^8$ with the proviso that at least two or three of $T^3$, $W^3$, $X^3$, $Y^3$ and $Z^3$ are $CH_2$-groups, $R^7$ and $R^8$ are independently a branched or unbranched $C_1$–$C_9$ alkyl chain, a branched or unbranched $C_2$–$C_9$ alkenyl chain, a branched or unbranched $C_2$–$C_9$ alkynyl chain, —$C_3$–$C_9$ cycloalkyl, $C_4$–$C_9$ cycloalkenyl or H, or pharmaceutically acceptable salts thereof.

The present invention further provides compounds of formula (I), wherein R' is

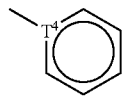

wherein $T^4$ is C or $N^+$, or pharmaceutically acceptable salts thereof.

The residues R' defined in the description and the claims may be mono- or poly-substituted by, e.g., alkyl, alkoxy, alkenyl, alkynyl, acyl, carbocyclic, aryl, heteroaryl, heterocyclic, thioether, $NO_2$, $NH_2$, F, Cl, Br, I atoms or groups, mono- or di-substitution being preferred. It is especially preferred that the substituents are not substituted any further.

Furthermore the present invention provides compounds of formula (I), wherein R' is an amino acid, a peptide or a dipeptide or a mimetic thereof.

The salts of the compounds of the invention may, assuming that they have basic properties, be in the form of inorganic or organic salts.

The compounds of the present invention can be converted into and used as acid addition salts, especially pharmaceutically acceptable acid addition salts. The pharmaceutically acceptable salt generally takes a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of the present invention are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

Compounds comprising acylated hydroxamates are new inhibitory structures. With their selectivity and stability they fulfil the requirements for the development of new drugs.

Throughout the description and the claims the expression "acyl" can denote a $C_{1-20}$ acyl residue, preferably a $C_{1-8}$ acyl residue and especially preferred a $C_{1-4}$ acyl residue, "carbocyclic" or "cycloalkyl" can denote a $C_{3-12}$ carbocyclic residue, preferably a $C_4$, $C_5$ or $C_6$ carbocyclic residue, "cycloalkenyl" can denote a $C_{3-12}$ carbocyclic residue, preferably a $C_5$ or $C_6$ carbocyclic residue having at least one double band at any desired location. "Heteroaryl" is defined as an aryl residue, wherein 1 to 4, preferably 1, 2 or 3 ring atoms are replaced by heteroatoms like N, S or O. "Heterocycloalkyl" or "heterocyclic" is defined as a cycloalkyl residue, wherein 1, 2 or 3 ring atoms are replaced by heteroatoms like N, S or O. "Heterocycloalkenyl" is defined as a heterocycloalkyl residue having at least one double bond at any desired location. The expression "alkyl" can denote a $C_{1-50}$ alkyl group, preferably a $C_{6-30}$ alkyl group, especially a $C_{8-12}$ alkyl group; an alkyl group may also be a methyl, ethyl, propyl, isopropyl or butyl group. The expression "aryl" is defined as an aromatic residue, preferably substituted or optionally unsubstituted phenyl, benzyl, naphthyl, biphenyl or anthracene groups, which preferably have 6–24, more preferred 8–14 C ring atoms; the expression "alkenyl" can denote a $C_{2-10}$ alkenyl group, preferably a $C_{2-6}$ alkenyl group, which has the double bond or the double bonds at any desired location and may be substituted or unsubstituted; the expression "alkynyl" can denote a $C_{2-10}$ alkynyl group, preferably a $C_{2-6}$ alkynyl group, which has the triple bond or the triple bonds at any desired location and may be substituted or unsubstituted; the expression "alkoxy" can denote a $C_{1-50}$ alkyl-oxygen group, preferably a $C_{1-6}$ alkyl-oxygen group; the expression "alkenyloxy" can denote a $C_{2-10}$ alkenyl-oxygen group, preferably a $C_{2-6}$ alkenyloxygen group; the expression "alkynyloxy" can denote a $C_{2-10}$ alkynyl-oxygen group, preferably a $C_{2-6}$ alkynyl-oxygen group; the expression "carbocyclicoxy" can denote a $C_{3-12}$ carbocyclic-oxygen group; the expression "heteroaryloxy" can denote a heteroaryl-oxygen group, the expression "heterocyclicoxy" can denote a heterocyclic-oxygen group; the expression "substituted" can denote any desired substitution by one or more, preferably one or two, alkyl, alkenyl, alkynyl, mono- or multi-valent acyl, alkoxy, alkoxyacyl, alkenyloxy, alkynyloxy, carbocyclicoxy, heteroaryloxy, heterocyclicoxy, alkoxyalkyl groups, any monoether or polyether containing identical or different alkyl, aryl, alkenyl, alkynyl, carbocyclic, heteroaryl, heterocyclic residues, or any monothioether or polythioether containing identical or different alkyl, aryl, alkenyl, alkynyl, carbocyclic, heteroaryl, heterocyclic residues; the afore-mentioned substituents may in turn have one or more (but preferably zero) alkyl, alkenyl, alkynyl, mono- or multi-valent acyl, alkoxyacyl or alkoxyalkyl groups as side groups which are preferably not substituted themselves. Organic amines, amides, alcohols or acids, each having from 8 to 50 C atoms, preferably from 10 to 20 C atoms, can have the formulae (alkyl)$_2$N— or alkyl-NH—, —CO—N(alkyl)$_2$ or —CO—NH(alkyl), -alkyl-OH or -alkyl-COOH.

The expression urethanes can denote a compound of the formula R—NH—CO—OR"", wherein R"" is a substituted alkyl, acyl, alkenyl, alkynyl, carbocyclic, heteroaryl, heterocyclic or aryl residues. R is identical to the residue R of formula I and is as defined for formula I. Preferred for R"" are unsubstituted or substituted alkyl residues, e.g. methyl, ethyl, tert-butyl, 2,2,2-trichloroethyl, 2-(trimethylsilyl) ethyl; unsubstituted or substituted alkenyl residues, e.g. allyl; unsubstituted or substituted aryl residues, e.g. phenyl, benzyl, 9-fluorenylmethyl.

All of the above residues or groups can—if possible—be branched or unbranched, unsubstituted or substituted with, e.g., 1, 2, 3, 4 or 5 substitutents, whereof 1 or 2 substituents are preferred.

The expression "peptide" for the definition of the residue R can denote any di-, tri-, tetra-, penta-, hexa-, or polypeptide. The peptide can be constituted of any amino acids or mimetics of amino acids or peptides.

The group AS—AS can be constituted of any two amino acids or mimetics thereof.

Examples of amino acids are:
aspartic acid (Asp), glutamic acid (Glu), arginine (Arg), lysine (Lys), histidine (His), glycine (Gly), serine (Ser) and cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-amino octanoic acid (Aoa), azetidine-(2)-carboxylic acid (Ace), pipecolic acid (Pip), 3-amino propionic, 4-amino butyric and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO), Acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethylcysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cis Hyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-Amino-4-cyanobutyric acid (Cba), cycloalkanecarboxylic acids.

Examples of ω-amino acids are e.g.: 5-Ara (a minoraleric acid), 6-Ahx (aminohexanoic acid), 8-Aoc (aminooctanoic acid), 9-Anc (aminovanoic acid), 10-Adc (aminodecanoic acid), 11-Aun (aminoundecanoic acid), 12-Ado (aminododecanoic acid).

Further amino acids are: indanylglycine (Igl), indoline-2-carboxylic acid (Idc), octahydroindole-2-carboxylic acid (Oic), diaminopropionic acid (Dpr), diaminobutyric acid (Dbu), naphtylalanine (1-Nal), (2-Nal), 4-aminophenylalanin (Phe(4-NH$_2$)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe(3,4-Cl$_2$)), 3-fluorophenylalanine (Phe(3-F)), 4-fluorophenylalanine (Phe(4-F)), 3,4-fluorophenylalanine (Phe(3,4-F$_2$)), pentafluorophenylalanine (Phe(F$_5$)), 4-guanidinophenylalanine (Phe(4-guanidino)), hormophenylalanine (hPhe), 3-jodophenylalanine (Phe(3-J)), 4-jodophenylalanine (Phe(4-J)), 4-methylphenylalanine (Phe(4-Me)), 4-nitrophenylalanine (Phe-4-NO$_2$)), biphenylalanine (Bip), 4-phosphonomethylphenylalanine (Pmp), cyclohexyglycine (Ghg), 3-pyridinylalanine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4,-tetrahydroisoquinolin-3-carboxylic acid (Tic), propargylglycine (Pra), 6-hydroxynorleucine (NU(6-OH)), homotyrosine (hTyr), 3-jodotyrosine (Tyr(3-J)), 3,5-dijodotyrosine (Tyr(3,5-J$_2$)), d-methyl-tyrosine (Tyr(Me)), 3-NO$_2$-tyrosine (Tyr(3-NO$_2$)), phosphotyrosine (Tyr(PO$_3$H$_2$)), alkylglycine, 1-aminoindane-1-carboxy acid, 2-aminoindane-2-carboxy acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly(NH$_2$)), diaminobutyric acid (Dab), 1,3-dihydro-2H-isoinole-carboxylic acid (Disc), homocylcohexylalanin (hCha), homophenylalanin (hPhe oder Hof, trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3,4-tetrahydronorharmane-3-carboxylic acid (Tpi), β-(2-thienyl)-alanine (Tha).

Proteinogenic amino acids are defined as natural protein-derived α-amino acids. Non-proteinogenic amino acids are defined as all other amino acids, which are not building blocks of common natural proteins.

Peptide mimetics per se are known to a person skilled in the art. They are preferably defined as compounds which have a secondary structure like a peptide and optionally further structural characteristics; their mode of action is largely similar or identical to the mode of action of the native peptide; however, their activity (e.g. as an antagonist or inhibitor) can be modified as compared with the native peptide, especially vis à vis receptors or enzymes. Moreover, they can imitate the effect of the native peptide (agonist). Examples of peptide mimetics are scaffold mimetics, non-peptidic mimetics, peptoides, peptide nucleic acids, oligopyrrolinones, vinylogpeptides and oligocarbamates. For the definitions of these peptide mimetics see Lexikon der Chemie, Spektrum Akademischer Verlag Heidelberg, Berlin, 1999.

The aim for using these mimetic structures is increasing the activity, increasing the selectivity to decrease side effects, protect the compound (drug) against enzymatic degradation for prolongation of the effect.

Further peptide mimetics are defined in J. Gante, Angew. Chemie, 1994, 106, 1780–1802; V. J. Hruby et al., Biopolymers, 1997, 219–266; D. Nöteberg et al., 2000, 43, 1705–1713.

The present invention further includes within its scope prodrugs of the compounds, provided herein. In general, such prodrugs will be functional derivatives of the compounds which are readily convertible in vivo into the desired therapeutically active compound. Thus, in these cases, the use of the present invention shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Such prodrugs can be cleaved and the active inhibitors can be released. This activation of the active inhibitors can be achieved both by chemical and enzymatic reactions. Esterases, proteases and peptidases serve to release the active inhibitors from the compounds according to the invention. Esterases, proteases and peptidases, which are suitable in such manner, are disclosed in WO 97/45117, U.S. Pat. Nos. 5,433,955, 5,614,379 and U.S. Pat. No. 5,624,894. Preferred proteases are aminopeptidases, dipeptidyl aminopeptidases, endoproteases, and endopeptidases. Especially preferred proteases for the release of the active inhibitors from the precursor of the present invention are aminopeptidase N, aminopeptidase P, pyroglutaminyl aminopeptidase, dipeptidyl peptidase IV and dipeptidyl peptidase IV-like enzymes. Such proteases and their specificity are described in:

Handbook of Proteolytic Enzymes, Eds. Barrett, A. J., Rawlings, N. D. and Woessner, J. F. Academic Press, New York 1998.

The present invention accordingly also uses the concept to stabilize e.g. unstable inhibitors by masking them in prodrug form. Thereby the properties of the active inhibitors can be modulated. For example, the prodrugs according to the invention have the advantage that the active inhibitors of DP I are released according to individual patients' needs. Moreover, this invention has the further advantage that each organism will release exactly that amount of active inhibitor that is necessary to inhibit that amount of DP I molecules, which is present in the body of the respective organism.

When a prodrug according to the invention interacts with an enzyme as mentioned above, it is cleaved by this enzyme and the active inhibitor is released. The active inhibitor will inhibit DP I so that DP I cannot cleave any further compounds for a defined time. In certain cases, e.g. when the enzyme cleaving the prodrugs is DP I, the remaining prodrugs are not degraded during a defined time and thus, constitute an inhibitor reservoir until the concentration of DP I molecules rises again or active inhibitor molecules are eliminated or inactivated.

To summarise, it may be stated that, using the prodrugs of the present invention, it is possible in a completely surprising manner:

1. to achieve increased action of the inhibitors;
2. to release the active inhibitors according to the patient's needs;
3. to release the active inhibitors in a temporally controlled manner;
4. to release the active inhibitors in a site-specific manner; and
5. to provide a reservoir of DP I inhibitors.

According to the invention, there are furthermore provided pharmaceutical compositions that comprise at least one compound according to the invention, optionally in combination with carriers and/or adjuncts etc. that are customary per se.

The compounds and compositions according to the invention can be used for the in vivo inhibition of the enzyme dipeptidyl peptidase I or of enzymes similar to DP I.

They can be used especially for the treatment of diseases of mammals that can be influenced by modulation of the DP I activity in various cells, tissues and organs.

They are especially suitable for the treatment of DP I-mediated malignant cell degeneration, immune diseases and metabolic diseases of humans.

The present invention further relates to the use of the compounds and compositions according to the invention for improving the wound-healing process and for the treatment of impaired wound-healing in humans.

The compounds may especially be in prodrug form and be used in prodrug form.

Biological Evaluation

The compounds provided herein are highly specific inhibitors of the cysteine protease DP I.

Selected compounds, based on the general formula (II) below, were tested concerning their inhibitory potential against DP I and for their cross-reactivity against three more cysteine proteases, namely cathepsin B, H, L and another dipeptidyl peptidase, dipeptidyl peptidase IV (DP IV). The $IC_{50}$ values of the tested compounds are given in table 1. The inhibitory potential of the compounds is shown in table 2 ($k_{inact}/K_i$).

TABLE 1

$IC_{50}$ values of the compounds of formula II

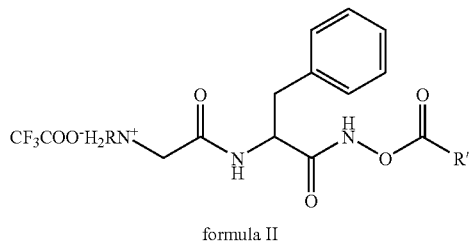

formula II

| com-pound | R | R' | DP I | Cath. B | Cath. H | Cath. L | DP IV |
|---|---|---|---|---|---|---|---|
| 10 | H | $CH_3$ | 0.258 | 117 | n.i. | 156 | n.i. |
| 11 | H | $C_6H_5$ | 0.034 | 37.7 | n.i. | 36.9 | n.i. |
| 12 | H | $C_6H_5$-p-$CH_3$ | 0.203 | 34.05 | 154 | 33.05 | n.i. |

TABLE 1-continued $IC_{50}$ values of the compounds of formula II

| com-pound | R | R' | DP I | Cath. B | Cath. H | Cath. L | DP IV |
|---|---|---|---|---|---|---|---|
| 13 | H | $C_6H_5$-p-$NO_2$ | 0.00262 | 5.31 | 34.7 | 7.32 | n.i. |
| 14 | $CH_3$ | $C_6H_5$ | 0.157 | 41.8 | 205 | 4.61 | n.i. | n.i. = no inhibition

Cytotoxicity Evaluation

The toxicological potential of the compounds provided therein against murine cell lines is different from their toxicological potential against human cell lines. Selected compounds, based on the general formula (II) above, were tested concerning their cytotoxicological potential against the two cell-lines, L-929 (murine fibroblast cell line) and Hep-G2 (human hepatocyte cell line) cells. The $LD_{50}$ values of the tested compounds are given in table 2.

TABLE 2

$LD_{50}$ values of the compounds

| compound | $k_{inact}/K_i$ [$M^{-1}s^{-1}$] | $LD_{50}$ [mg * $ml^{-1}$] | |
|---|---|---|---|
| | | L-929 | Hep-G2 |
| 10 | $3.9 * 10^4$ | 4.3 | 1.6 |
| 11 | $4 * 10^5$ | 1.0 | 0.8 |
| 12 | $1.9 * 10^4$ | n.d. | n.d. |
| 13 | $7.9 * 10^4$ | 2.3 | 0.8 |
| 14 | $1.4 * 10^5$ | n.d. | n.d. | n.d. = not determined

Synthesis

The inhibitors 10–14 were prepared as described in Scheme 1. The dipeptides 1 and 2 were prepared starting from HCl*H-Phe-OMe and Boc-Gly-OH or Boc-Sar-OH respectively (obtained from Bachem) according to a procedure described in Bodansky, M. and Bodansky, A. (Method A).

The dipeptides were converted into the peptidylhydroxylamines 3 and 4 by treatment with hydroxylamine (Method B). Acylation with various carbonic acid chlorides in the presence of triethylamine gave the corresponding acetyl derivatives 5–9 (Method C). Treatment of the compounds 5–9 with trifluoroacetic acid provided the inhibitors 10–14 (Method D).

Scheme 1. Synthesis of the compounds 1–14

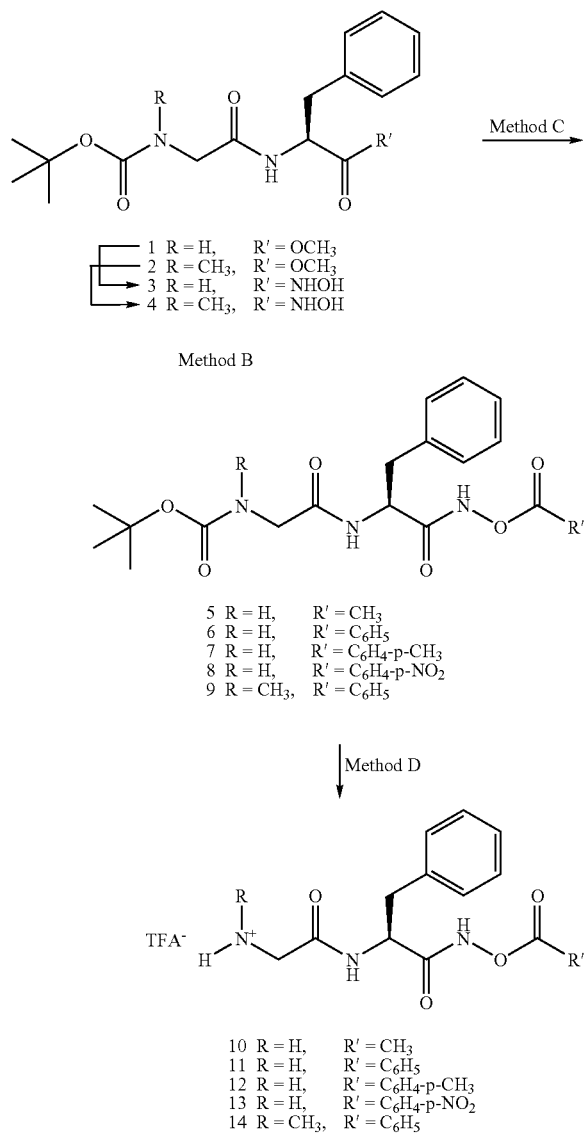

Experimental

NMR spectra were performed on Varian Unity 500 and Bruker AM 400 spectrometers. The following abbrevations are used: s, singlet; d, doublet; t, triplet; q, quartet; br., broad. Melting points were measured on a Leica Galen III melting point apparatus and are uncorrected. ESI-MS: Mass spectra were taken with an MDS Sciex API 365 mass spectrometer equipped with an Ionspray™ interface (MDS Sciex; Thorn Hill, ON, Canada). The instrument settings, data acquisition and processing were controlled by the Applied Biosystems (Foster City, Calif., USA) Analyst™ software for Windows NT™. 50–100 scans were performed by the positive ionization Q1 scan mode to accumulate the peaks. Sample solutions were diluted with 50% methanol in 0.5% formic acid to reach concentrations about 10 µg/ml. Each sample solution was introduced directly by a microsyringe (1 ml) through an infusion pump (Havard Apperatus 22; Havard Instruments; Holliston, Mass., USA) and fused silica capillary tubing at a rate of 20 µl/min. Thin layer chromatography (TLC) was done with Macherey Nagel Polygram® SIL G/UV$_{245}$. Visualisation was accomplished by means of UV light at 254 nm, followed by dyeing with potassium permanganate or ninhydrin. Solvents were distilled prior to use. Petroleum ether with a boiling range of 35–65° C. was used. All commercially available reagents were used without further purification. Amino acid derivates were obtained from Bachem. For the purification a preparative HPLC [acetonitrile-water, gradient: 5–95%, flow rate: 6 ml min$^{-1}$, column: Nucleosil 7µ C18 100A, 250×21.2 mm (phenomenex), pump: L-6250 Merck-Hitachi] was used.

Abbrevations

Ac: Acetyl (COCH$_3$), Bz: Benzoyl (COC$_6$H$_5$), CAIBE: Isobutyl chloroformate, NMM: N-Methylmorpholine, PE: Petroleum ether.

General Methods

Method A (Preparation of the dipeptides): HCl*H-L-Phe-OMe and Boc-Gly-OH or Boc-Sar-OH were coupled according to the method of Bodansky, M. and Bodansky, A., The Practice of Peptide Synthesis 2$^{nd}$ Edition, Springer-Verlag. To a stirred solution of Boc-Gly-OH or Boc-Sar-OH (17.1 mmol, 1.0 equiv) in 75 ml dry THF was added NMM (1.88 ml, 17.1 mmol, 1.0 equiv). After cooling the mixture to −15° C. CAIBE (2.22 ml, 17.1 mmol, 1.0 equiv) was added and after stirring for further 15 min HCl*H-L-Phe-OMe (3.69 g, 17.1 mmol, 1.0 equiv) and NMM (1.88 ml, 17.1 mmol, 1.0 equiv) were added. The mixture was stirred for 14 h, during which time it was allowed to warm to room temperature. The solvent was evaporated in vacuo and the obtained residue was dissolved in ethyl acetate (50 ml), washed with 1 N HCl, water, aqueous NaHCO$_3$, and brine (30 ml per washing step). The organic layer was dried over Na$_2$SO$_4$, filtered and concentrated under reduced pressure. The product was crystallized by means of ethyl acetate/pentane and used without further characterization.

Method B (Conversation into the peptidylhydroxylamines): The peptidylhydroxylamines were prepared according to the method of Brömme, D., Demuth, H. U., N,O-Diacyl hydroxamates as selective and irreversible inhibitors of cysteine proteinases. *Methods in Enzym.* 244, 671–685. Hydroxylamine hydrochloride (827 mg, 11.9 mmol, 4.0 equiv) was dissolved in 18 ml of dry methanol. 17 ml of fresh prepared NaOMe solution (3.5 M in absolute methanol) was added dropwise. The mixture was filtered after 20 min of stirring and the filtrate was dropped into a chilled and stirred solution of the dipeptide (2.97 mmol, 1.0 equiv) in 4 ml of dry methanol. After 8 h of stirring at 0° C. the solvent was removed and the remaining oil was taken up in 3 ml of water and extracted with 3 ml of ethyl acetate. The aqueous phase was brought to a pH-value of 3 by means of adding KHSO$_4$ and again extracted three times by means of 15 ml ethyl acetate. The organic layer was dried over Na$_2$SO$_4$, filtered and evaporated. The residue was recrystalized by means of MeOH/pentane.

Method C (Acylation): To a stirred solution of a peptidylhydroxylamine (2 mmol, 1.0 equiv) in a mixture of dry THF (5 ml) and dry DMF (3 ml) at −15° C. was added triethylamine (20.0 µl, 2.2 mmol, 1.1 equiv) and the corresponding carbonic acid chlorides (2.1 mmol, 1.05 equiv) dissolved in dry THF (4 ml). This solution was stirred for 4 hours at −5° C. before the solvents were removed under reduced pressure. The obtained residue was washed with cold KHSO$_4$ (5% in water, 5 ml). The precipitate was dissolved in ethyl acetate (10 ml) and dried over Na$_2$SO$_4$.

After filtration the solvent was evaporated under reduced pressure and the remaining residue was recrystallized by means of MeOH/PE.

Method D (Deprotecting the boc protecting group): The Boc-protected compound (2 mmol) was dissolved in trifluoroacetic acid (10 ml) and the solution was stirred for 1.5 h at room temperature before it was diluted with toluol (3 ml). The solvents were removed under reduced pressure and the obtained residue was triturated with $Et_2O$ (10 ml) and filtered. The resulted solid was washed three times with $Et_2O$ (5 ml) and dried. The obtained residue was purified by flash chromatography to give the desired compound.

Starting Material

Synthesis of Boc-Gly-L-Phe-OMe (1)

Boc-Gly-L-Phe-OMe (1) was prepared according to Method A in a yield of 98%.—TLC ($MeOH/CHCl_3$, 1:9): $R_f$=0.71.—$^1$H NMR (500 MHz, DMSO-$d_6$): δ=1.36 (s, 9 H, t-Bu), 2.90 (dd, 1 H, J=13.7 Hz, J=8.7 Hz, $CH_2$ Phe), 3.00 (dd, 1 H, J=13.7 Hz, J=8.7 Hz, $CH_2$ Phe), 3.58 (s, 3 H, $OCH_3$), 4.01 (q, 2 H, J=7.1 Hz, $CH_2Gly$), 4.46 (dd, 1 H, J=13.7 Hz, J=8.1 Hz, CH Gly), 6.90 (t, 1 H, J=6.0 Hz, NH), 7.17–7.22 (m, 3 H, aryl-H), 7.25–7.28 (m, 2 H, aryl-H), 8.20 (d, 1 H, J=7.6 Hz, NH).—MS (EI) m/z (%): 337 [M+H$^+$], 354 [M+NH$_4^+$], 359 [M+Na$^+$], 375 [M+K$^+$].

Synthesis of Boc-Sar-L-Phe-OMe (2)

Boc-Sar-L-Phe-OMe (2) was prepared according to Method A in a yield of 99%.—TLC ($MeOH/CHCl_3$, 1:9): $R_f$=0.82.—MS (EI) m/z (%): 351 [M+H$^+$], 368 [M+NH$_4^+$], 373 [M+Na$^+$], 389 [M+K$^+$].

Synthesis of Boc-Gly-L-Phe-NHOH (3)

Boc-Gly-L-Phe-NHOH (3) was prepared according to Method B in a yield of 72%.—TLC. ($MeOH/CHCl_3$, 1:9): $R_f$=0.44.—$^1$H NMR (500 MHz, DMSO-$d_6$): δ=1.36 (s, 9 H, t-Bu), 2.77 (dd, 1 H, J=13.7 Hz, J=8.9 Hz, $CH_2$ Phe), 2.91 (dd, 1 H, J=13.7 Hz, J=8.3 Hz, $CH_2Phe$), 3.41 (dd, 1 H, J=16.7 Hz, J=6.2 Hz, $CH_2Gly$), 3.53 (dd, 1 H, J=16.7 Hz, J=6.2 Hz, $CH_2Gly$), 4.34–4.38 (m, 1 H, CH Phe), 6.86 (t, 1 H, J=6.1 Hz, NH), 7.16–7.19 (m, 3 H, aryl-H), 7.23–7.28 (m, 2 H, aryl-H), 8.06 (d, 1 H, J=8.5 Hz, NH), 8.88 (s, 1 H, OH), 10.65 (s, 1 H, NH).—MS (EI) m/z (%): 338 [M+H$^+$], 355 [M+NH$_4^+$], 360 [M+Na$^+$], 376 [M+K$^+$].

Synthesis of Boc-Sar-L-Phe-NHOH (4)

Boc-Sar-L-Phe-NHOH (4) was prepared according to Method B in a yield of 88%.—TLC ($MeOH/CHCl_3$, 1:9): $R_f$=0.35.—MS (EI) m/z (%): 352 [M+H$^+$], 369 [M+NH$_4^+$], 374 [M+Na$^+$], 390 [M+K$^+$].

Synthesis of Boc-Gly-L-Phe-NHO-Ac (5)

Boc-Gly-L-Phe-NHO-Ac (5) was prepared according to Method C in a yield of 62%.—TLC ($MeOH/CHCl_3$, 1:9): $R_f$=0.69.—$^1$H NMR (500 MHz, DMSO-$d_6$): δ=1.35 (s, 9 H, t-Bu), 2.14 (s, 3 H, $CH_3$), 2.80 (dd, 1 H, J=13.7 Hz, J=9.6 Hz, $CH_2$ Phe), 2.98 (dd, 1 H, J=13.7 Hz, J=,9.8 Hz, $CH_2$ Phe), 3.42 (dd, 1 H, J=16.9 Hz, J=6.2 Hz, $CH_2$ Gly), 3.54 (dd, 1 H, J=16.9 Hz, J=6.2 Hz, $CH_2$ Gly), 4.50–4.54 (m, 0.1 H, CH Phe), 6.85 (t, 1 H, J=6.1 Hz, NH), 7.17–7.27 (m, 5 H, aryl-H), 8.18 (d, 1 H, J=8.4 Hz, NH), 12.00 (s, 1 H, NH).—MS (EI) m/z (%): 380 [M+H$^+$], 397 [M+NH$_4^+$], 402 [M+Na$^+$], 418 [M+K$^+$].

Synthesis of Boc-Gly-L-Phe-NHO-Bz (6)

Boc-Gly-L-Phe-NHO-Bz (6) was prepared according to Method C in a yield of 48%.—TLC ($MeOH/CHCl_3$, 1:9): $R_f$=0.66.—MS (EI) m/z (%): 442 [M+H$^+$], 459 [M+NH$_4^+$], 464 [M+Na$^+$], 480 [M+K$^+$].

Synthesis of Boc-Gly-L-Phe-NHO-Bz-p-CH$_3$ (7)

Boc-Gly-L-Phe-NHO-Bz-p-CH$_3$ (7) was prepared according to Method C in a yield of 52%.—TLC ($MeOH/CHCl_3$, 1:9): $R_f$=0.55.—MS (EI) m/z (%): 456 [M+H$^+$], 473 [M+NH$_4^+$], 478 [M+Na$^+$], 494 [M+K$^+$].

Synthesis of Boc-Gly-L-Phe-NHO-Bz-p-NO$_2$ (8)

Boc-Gly-L-Phe-NHO-Bz-p-NO$_2$ (8) was prepared according to Method C in a yield of 62%.—TLC ($MeOH/CHCl_3$, 1:9): $R_f$=0.57.—MS (EI) m/z (%): 487 [M+H$^+$], 504 [M+NH$_4^+$], 509 [M+Na$^+$], 525 [M+K$_+$].

Synthesis of Boc-Sar-L-Phe-NHO-Bz (9)

Boc-Sar-L-Phe-NHO-Bz (9) was prepared according to Method C in a yield of 78%.—TLC ($MeOH/CHCl_3$, 1:9): $R_f$=0.62.—MS (EI) m/z (%): 456 [M+H$^+$], 473 [M+NH$_4^+$], 478 [M+Na$^+$], 494 [M+K$^+$].

Pharmaceutical Compositions

Additionally, the present invention includes the use of the compounds provided herein for the preparation of a medicament for the treatment of a condition mediated by modulation of the DP I activity in a subject. The compound may be administered to a patient by any conventional route of administration, including, but not limited to, intravenous, oral, subcutaneous, intramuscular, intradermal, parenteral and topical. Especially preferred is topical administration.

The present invention also provides pharmaceutical compositions comprising one or more compounds of this invention in association with a pharmaceutically active carrier.

To prepare the pharmaceutical compositions of this invention, one or more active compounds or salts thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. For topical formulations, such as creams, gels etc., the carrier will usually comprise glycerolmonostearate, cetyl alcohol, triglycerides, vaseline, propylenglycole, water and paraffins.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg/bw (preferred 0.1–30 mg/kg/bw) and may be given at a dosage of from about 0.1–300 mg/kg/day/bw (preferred 1–50 mg/kg/day/bw). The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 500 mg of the active ingredient of the present invention.

The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose-acetate.

This liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

Most preferred according to this invention are formulations for topical administration of the compounds provided herein, such as creams, gels and sprays. Suitable carriers for topical administration include glycerolmonostearate, cetyl alcohol, triglycerides, vaseline, propylenglycole, water or paraffins.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The method of treating conditions modulated by DP I described in the present invention may also be carried out using a pharmaceutical composition comprising any of the compounds as defined herein and a pharmaceutically acceptable carrier. The pharmaceutical composition may contain between about 0.01 mg and 500 mg, preferably about 5 to 50 mg, of the compound, and may be formulated into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions. Formulations or topical administration include creams, gels, sprays etc.

Advantageously, compounds of the present invention may be administered in a single daily dose, or the total daily dosage may be administered in divided doses of two, three or four times daily. Furthermore, compounds for the present invention can be administered in intranasal-form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen. Preferably, the compounds of the present invention are administered topically.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles.

Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can—include polyvinylpyrrolidone, pyran copolymer, polyhydroxypropylmethacrylamidephenol, olyhydroxyethylaspartamidephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of the addressed disorders is required.

The daily dosage of the products may be varied over a wide range from 0.01 to 1.000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.1 mg to about 500 mg per adult human per day. Preferably, the range is from about 1 to about 250 mg per adult human per day.

For topical administration, the compositions are preferably provided in the form of creams, gels or sprays, containing from about 0.01 to 10%, preferably 0,1 to 10%, most preferably 1 to 10% of the active ingredient.

Examples of typical creams for topical administration are listed below.

| 1. Basic cream DAC | Glycerolmonostearate 60 | 4.0 g |
|---|---|---|
| | Cetylalcohol | 6.0 g |
| | Mid sized triglycerides | 7.5 g |
| | Vaseline | 25.5 g |
| | Macrogel-1000-glycerolmonostearate | 7.0 g |
| | Propylenglycol | 10.0 g |
| | Water | 40.0 g |
| 2. Eucerin cum aqua | Lanolin wax alcohol cream | 50.0 g |
| | Water | 50.0 g |

The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

For oral administration, the compounds or compositions of the present invention may be taken before a meal, while taking a meal or after a meal.

When taken before a meal, the compounds or compositions of the present invention can be taken 1 hour, preferably 30 or even 15 or 5 minutes before eating.

When taken while eating, the compounds or compositions of the present invention can be mixed into the meal or taken in a separate dosage form as described above.

When taken after a meal, the compounds and compositions of the present invention can be taken 5, 15, or 30 minutes or even 1 hour after finishing a meal.

EXAMPLES

Example 1

Synthesis of TFA*H-Gly-L-Phe-NHO-Ac (10)

TFA*H-Gly-L-Phe-NHO-Ac (10) was prepared according to Method D. The compound was purified by flash chromatography to give the product as a white solid (93%) of m.p. 71–73° C.—TLC (n-BuOH/ethyl acetate/water/acetic acid, 1:1:1:1): $R_f$=0.73.—$^1$H NMR (400 MHz, DMSO-$d_6$): δ=2.16 (s, 3 H, $CH_3$), 2.80 (dd, 1 H, J=14.0 Hz, J=9.7 Hz, $CH_2$Phe), 3.04 (dd, 1 H, J=13.9 Hz, J=9.6 Hz, $CH_2$ Phe), 3.40 (d, 1 H, J=16.3 Hz, $CH_2$ Gly), 3.55 (d, 1 H, J=16.3 Hz, $CH_2$ Gly), 4.58–4.64 (m, 1 H, CH Phe), 7.19–7.30 (m, 5 H, aryl-H), 8.84 (d, 1 H, J=8.4 Hz, NH).—MS (EI) m/z (%): 280 [M+H$^+$].

Example 2

Synthesis of TFA*H-Gly-L-Phe-NHO-Bz (11)

TFA*H-Gly-L-Phe-NHO-Bz (11) was prepared according to Method D. The compound was purified by flash chromatography to give the product as a white solid (66%) of m.p. 75–80° C.—TLC (n-BuOH/ethyl acetate/water/acetic acid, 1:1:1:1): $R_f$=0.81.—$^1$H NMR (500 MHz, DMSO-$d_6$): δ=2.86 (dd, 1 H, J=13.9 Hz, J=10.0 Hz, $CH_2$ Phe), 3.13 (dd, 1 H, J=13.9 Hz, J=9.9 Hz, $CH_2$ Phe), 3.43 (d, 1 H, J=16.3 Hz, $CH_2$ Gly), 3.58 (d, 1 H, J=16.3 Hz, $CH_2$ Gly), 4.68–4.72 (m, 1 H, CH Phe), 7.21–7.25 (m, 1 H, aryl-H), 7.26–7.31 (m, 4 H, aryl-H), 7.58–7.63 (m, 2 H, aryl-H), 7.74–7.77 (m, 1 H, aryl-H), 7.93–8.03 (m, 2 H, aryl-H), 7.94 (s, br., 3 H, $NH_3^+$), 8.91 (d, 1 H, J=8.3 Hz, NH), 12.46 (s, br., 1 H, NH).—MS (EI) m/z (%): 342 [M+H$^+$].

Example 3

Synthesis of TFA*H-Gly-L-Phe-NHO-Bz-p-CH (12)

TFA*H-Gly-L-Phe-NHO-Bz-p-$CH_3$ (12) was prepared according to Method D. The compound was purified by flash chromatography to give the product as a white solid (82%) of m.p. 98–101° C.—TLC (n-BuOH/ethyl acetate/water/acetic acid, 1:1:1:1): $R_f$=0.75.—$^1$H NMR (400 MHz, DMSO-$d_6$): δ=2.41 (s, 3 H, $CH_3$), 2.85 (dd, 1 H, J=13.7 Hz, J=10.0 Hz, $CH_2$Phe), 3.12 (dd, 1 H, J=12.9 Hz, J=10.0 Hz, $CH_2$ Phe), 3.42 (d, 1 H, J=15.8 Hz, $CH_2$ Gly), 3.58 (d, 1 H, J=16.0 Hz, $CH_2$ Gly), 4.664.72 (m, 1 H, CH Phe), 7.21–7.25 (m, 1 H, aryl-H), 7.27–7.31 (m, 4 H, aryl-H), 7.40 (d, 2 H, J=8.0 Hz, aryl-H), 7.90 (d, 2 H, J=8.2 Hz, aryl-H), 7.94 (s, br., 3 H, $NH_3^+$), 8.90 (d, 1 H, J=8.4 Hz, NH), 12.40 (s, br., 1 H, NH).—MS (EI) m/z (%): 356 [M+H$^+$].

Example 4

Synthesis of TFA*H-Gly-L-Phe-NHO-Bz-p-$NO_2$ (13)

TFA*H-Gly-L-Phe-NHO-Bz-p-$NO_2$ (13) was prepared according to Method D. The compound was purified by flash chromatography to give the product as a white solid (32%) of m.p. 80–85° C.—TLC (n-BuOH/ethyl acetate/water/acetic acid, 1:1:1:1): $R_f$=0.77.—$^1$H NMR (400 MHz, DMSO-$d_6$): δ=2.86 (dd, 1 H, J=13.9 Hz, J=9.8 Hz, $CH_2$ Phe), 3.12 (dd, 1 H, J=13.9 Hz, J=9.6 Hz, $CH_2$ Phe), 3.44 (d, 1 H, J=16.6 Hz, $CH_2$ Gly), 3.58 (d, 1 H, J=16.6 Hz; $CH_2$ Gly), 4.68–4.74 (m, 1 H, CH Phe), 7.21–7.26 (m, 1 H, aryl-H), 7.28–7.32 (m, 4 H, aryl-H), 7.94 (s, br., 3 H, $NH_3^+$), 8.25 (d, 2 H, J=8.9 Hz, aryl-H), 8.39 (d, 2 H, J=8.9 Hz, aryl-H), 8.93 (d, 1 H, J=8.4 Hz, NH), 12.69 (s, br., 1 H, NH).—MS (EI) m/z (%): 387 [M+H$^+$].

Example 5

Synthesis of TFA*H-Sar-L-Phe-NHO-Bz (14)

TFA*H-Sar-L-Phe-NHO-Bz (14) was prepared according to Method D. The compound was purified by flash chromatography to give the product as a white solid (82%) of m.p. 69–71° C.—TLC (n-BuOH/ethyl acetate/water/acetic acid, 1:1:1:1): $R_f$=0.64.—$^1$H NMR (400 MHz, DMSO-$d_6$): δ=2.45 (s, 3 H, $CH_3$), 2.86 (dd, 1 H, J=13.9 Hz, J=10.3 Hz, $CH_2$Phe), 3.14 (dd, 1 H, J=13.9 Hz, J=10.3 Hz, $CH_2$ Phe), 3.58 (d, 1 H, J=16.1 Hz, $CH_2$ Gly), 3.72 (d, 1 H, J=16.1 Hz, $CH_2$ Gly), 4.69–4.75 (m, 1 H, CH Phe), 7.20–7.26 (m, 1 H, aryl-H), 7.28–7.33 (m, 4 H, aryl-H), 7.60 (t, 2 H, J=7.8 Hz, aryl-H), 7.76 (t, 1 H, J=6.8 Hz, aryl-H), 8.02 (d, 2 H, J=7.0 Hz, aryl-H), 8.63 (s, br., 2 H, $NH_2^+$), 9.02 (d, 1 H, J=8.6 Hz, NH), 12.48 (s, br., 1 H, NH).—MS (EI) m/z (%): 356 [M+H$^+$].

Example 6

Biological Evaluation

Spectrophotometric Assay:

DP I was obtained from Qiagen. The DP I activity was determined in a continous spectrophotometric rate assay using the substrate HCl*Gly-L-Arg-pNA (obtained from Bachem, λ=405 nm) on a HTS 7000 plus microplate reader (PerkinElmer; Überlingen, Germany). The assay was performed at 30° C., using a MES-buffered system (pH 5.6, 0.104 M (2-[4-Morpholino]ethanesulphonic acid)hydrat/ 0.0104 M KCl) containing 0.0104 M dithiothreitol and 0.0052 M EDTA. The obtained data were analyzed with the enzyme kinetic calculation program Grafit 4.016 (Erithacus Ltd, UK).

Example 7

Determination of $k_i$-Values

For the $K_i$-value determination a UV-spectrophotometer (Lambda 20, PerkinElmer, Überlingen, Germany) was used. The reaction was monitored via the p-nitroaniline released from the substrate (Gly-Arg-pNA) at λ=390 nm. DP I (1 U/mg, assay condition: Tagzyme handbook, Qiagen, Hilden, Germany) was diluted in MES-buffer (1:1000) and preincubated and activated for 30 min on crashed ice. The reaction mixture consists: 500 µl stock solution MES-buffer, 500 µl HCl*Gly-L-Arg-pNA, 250 µl inhibitor, 50 µl DP I. In order to calculate the second order rate constant ($k_{inact}/K_i$) two substrate concentrations (1 mM and 0.5 mM in the incubation mixture) were combined with 6 inhibitor concentrations ($5*10^{-7}$ M to $3*10^{-8}$ M in the assay). From the product-time-course the observed first order rate constant was determined.

$$A \xrightarrow{k_{obs}} P$$

$$v = -\frac{d[A]}{d[t]} = \frac{d[P]}{d[t]} = k_{obs} * [A]$$

Plotting $1/k_{obs}$ versus substrate concentration allows the calculation of the real first order rate constant of inactivation for each inhibitor concentration at [S]=0.

$$k = \frac{k_{inact} * [I]}{K_i + [I]}$$

$K_i$ dissociation constant of the enzyme-inhibitor complex
$k_{inact}$ inactivation rate constant
A substrate
P product
[S] substrate concentration
[I] inhibitor concentration Based on this equation $K_i$ and $k_{inact}$ can be determined.

Example 8

Cytotoxicity Assay

HEP-G2, a human hepatocyte cell line (ACC180) and L-929, a mouse fibroplast cell line (ACC2) were grown in RPMI 1604 with 10% fetal bovine serum and 60 µg/ml gentamycin.

All cultures were fed every 2–3 days and incubated in an humified chamber at 37° C. and 5% $CO_2$. For determining the cytotoxicity of different DPI-inhibitors, we used the CytoTox96™ Non-radioactive Cytotoxicity Assay (Promega, Madison, Wis., USA). HEP-G2 (30000 cells per well) and L-929 (20000 cells per well) were placed in 96 well plates in RPMI 1604 with 10% fetal bovine serum and grown for 24 hours. The cells were then incubated with various concentrations of different DPI-inhibitors for 24 hours in RPMI 1604 with 10% fetal bovine serum. One hour after addition of MTS-solution, the reaction was stopped by adding stop-solution of Promega. The absorbance was measured at 490 nm with a spectrophotometer. All experiments were performed twice simultaneously in three wells.

What is claimed is:

1. A pharmaceutically acceptable salt of a compound of the general formula (I)

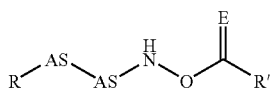

formula (I)

wherein

R is H or a peptide or a branched or unbranched $C_1$–$C_9$ alkyl chain, a branched or unbranched $C_2$–$C_9$ alkenyl chain, a branched or unbranched $C_2$–$C_9$ alkynyl chain, a $C_3$–$C_9$ cycloalkyl, $C_4$–$C_9$ carbocyclic, $C_5$–$C_{14}$ aryl, $C_3$–$C_9$ heteroaryl, or $C_3$–$C_9$ heterocyclic, all of the above residues optionally being substituted, the residue AS—AS is a dipeptide or a mimetic thereof, with the proviso that AS—AS may not be Ala-Pro, Ala-Pro mimetic, Ile-Pro or Tyr-Gly, E is O or S, and R' is a branched or unbranched $C_1$–$C_9$ alkyl chain, a branched or unbranched $C_2$–$C_9$ alkenyl chain, a branched or unbranched $C_2$–$C_9$ alkynyl chain, a $C_3$–$C_9$ cycloalkyl, $C_4$–$C_9$ cycloalkenyl, $C_2$–$C_9$ heterocycloalkyl, $C_3$–$C_9$ heterocycloalkenyl, $C_5$–$C_{14}$ aryl, $C_3$–$C_9$ heteroaryl, or $C_3$–$C_9$ heterocyclic, wherein the heterocycloalkyl, heterocycloalkenyl, heteroaryl, heterocyclic residue can have up to 6 hetero atoms in the ring, or R' is an amino acid or a peptide or a mimetic thereof, all of the above residues optionally being substituted, or R' is H or alkoxy, alkenyloxy, alkynyloxy, carbocyclicoxy, heteroaryloxy, heterocyclicoxy, thioether or a substituted residue thereof, with the proviso, that the compound H-Gly-Phe-NHO—BZ including all pharmaceutically acceptable salts thereof are excluded.

2. The pharmaceutically acceptable salt according to claim 1, wherein R is phenyl or naphthyl optionally mono-, di-, or poly-substituted by $C_1$–$C_6$ alkoxy, $C_1$–$C_6$ alkyl, $C_2$–$C_6$ alkenyloxy, $C_2$–$C_6$ alkynyloxy, $C_3$–$C_9$ heteroaryloxy, $C_3$–$C_9$ heterocyclicoxy, $C_1$–$C_6$ thioether or a substituted residue thereof, $NO_2$, $NH_2$, F, Cl, Br, 1 atoms or groups.

3. The pharmaceutically acceptable salt according to claim 1, wherein R' is a phenyl or naphthyl.

4. The pharmaceutically acceptable salt according to claim 1, wherein R' is

wherein V is N or CH and n=1–6.

5. The pharmaceutically acceptable salt according to claim 1, wherein R' is

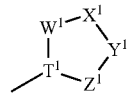

wherein $T^1$ is CH or N, $W^1$, $X^1$, $Y^1$ and $Z^1$ are independently from each other selected from $CH_2$, $NR^2$, $N^+(R^3)_2$, O, S, SO, $S(R^4)_2$, $SO_2$, with the proviso that at least two of $W^1$, $X^1$, $Y^1$ and $Z^1$ are $CH_2$-groups, $R^2$, $R^3$ and $R^4$ are independently from each other a branched or unbranched $C_2$–$C_9$ alkyl chain, a branched or unbranched $C_2$–$C_9$ alkenyl chain, a branched or unbranched $C_2$–$C_9$ alkynyl chain, $C_3$–$C_9$ cycloalkyl, $C_4$–$C_9$ cycloalkenyl or H.

6. The pharmaceutically acceptable salt according to claim 1, wherein R' is

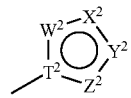

wherein $T^2$ is C or $N^+$, $W^2$, $X^2$, $Y^2$ and $Z^2$ are independently from each other selected from CH, $N^+$, $N^+R^5$ or $S^+R^6$, $R^5$ and $R^6$ are independently from each other a branched or unbranched $C_1$–$C_9$ alkyl chain, a branched or unbranched $C_2$–$C_9$ alkenyl chain, a branched or unbranched $C_2$–$C_9$ alkynyl chain, $C_3$–$C_9$ cycloalkyl, $C_4$–$C_9$ cycloalkenyl or H.

7. The pharmaceutically acceptable salt according to claim 1, wherein R' is

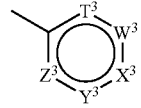

wherein $T^3$, $W^3$, $X^3$, $Y^3$ and $Z^3$ are independently from each other are selected from CH, $N^+N^+R^7$ or $S^+R^8$, $R^7$ and $R^8$ are independently from each other a branched or unbranched $C_1$–$C_9$ alkyl chain, a branched or unbranched $C_2$–$C_9$ alkenyl chain, a branched or unbranched $C_1$–$C_9$ alkynyl chain, $C_1$–$C_9$ cycloalkyl, $C_4$–$C_9$ cycloalkenyl or H.

8. The pharmaceutically acceptable salt according to claim 1, wherein R' is

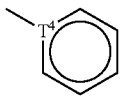

wherein $T^4$ is C or N.

9. The pharmaceutically acceptable salt according to claim 1, wherein R' is an amino acid, a peptide, a dipeptide or a mimetic thereof.

10. The pharmaceutically acceptable salt according to claim 1, wherein the residue R' may be mono-, di-, or poly-substituted by $C_1$–$C_6$ alkoxy, $C_1$–$C_6$ alkyl, $C_1$–$C_6$ thioether, $NO_2$, $NH_2$, F, Cl, Br, I atoms or groups, except when R' is H.

11. The pharmaceutically acceptable salt according to claim 1, wherein said compound is in the form of prodrugs.

12. A pharmaceutical composition comprising the pharmaceutically acceptable salt according to claim 1 and at least one pharmaceutically acceptable carrier and/or adjunct.

13. A method of treatment of a disease of a mammal comprising the step of administering to said mammal a therapeutically effective amount of the pharmaceutically acceptable salt according to claim 1 causing a modulation of the activity of DPI and/or DP I-like enzymes of said mammal.

14. A method of treatment of a disease of a mammal comprising the step of administering to said mammal a therapeutically effective amount of said pharmaceutical composition according to claim 12 causing a modulation of the activity of DPI and/or DP I-like enzymes of said mammal.

15. The method according to claim 13, wherein said modulation comprises the inhibition of DP I and/or DP I-like enzymes.

16. The method according to claim 13, wherein said disease is selected from the group consisting of malignant cell degeneration, immune diseases and metabolic diseases of humans.

17. The method according to claim 13, wherein said disease is impaired wound-healing in humans.

18. The method according to claim 14, wherein said modulation comprises the inhibition of DP I and/or DP I-like enzymes.

19. The method according to claim 18, wherein said disease is selected from the group consisting of malignant cell degeneration, immune diseases and metabolic diseases of humans.

20. The method according to claim 18, wherein said disease is impaired wound-healing in humans.

* * * * *